US011464873B2

(12) United States Patent
Zamore et al.

(10) Patent No.: US 11,464,873 B2
(45) Date of Patent: *Oct. 11, 2022

(54) RNA-MODULATING AGENTS

(71) Applicant: UNIVERSITY OF MASSACHUSETTS, Boston, MA (US)

(72) Inventors: Phillip D. Zamore, Northboro, MA (US); Jennifer Broderick, Worcester, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/722,762

(22) Filed: Dec. 20, 2019

(65) Prior Publication Data
US 2020/0268905 A1 Aug. 27, 2020

Related U.S. Application Data

(63) Continuation of application No. 14/866,186, filed on Sep. 25, 2015, now Pat. No. 10,556,020.

(60) Provisional application No. 62/055,759, filed on Sep. 26, 2014.

(51) Int. Cl.
C12N 15/11 (2006.01)
A61K 48/00 (2006.01)
C12N 15/113 (2010.01)
C12N 15/115 (2010.01)

(52) U.S. Cl.
CPC ........ A61K 48/0058 (2013.01); C12N 15/111 (2013.01); C12N 15/113 (2013.01); C12N 15/115 (2013.01); C12N 2310/11 (2013.01); C12N 2310/113 (2013.01); C12N 2310/16 (2013.01); C12N 2310/315 (2013.01); C12N 2310/3519 (2013.01); C12N 2320/30 (2013.01); C12N 2320/31 (2013.01); C12N 2320/32 (2013.01); C12N 2320/51 (2013.01); C12N 2320/53 (2013.01); C12N 2330/10 (2013.01); C12Q 2600/178 (2013.01)

(58) Field of Classification Search
CPC .. C12N 15/111; C12N 15/113; C12N 2310/11
See application file for complete search history.

(56) References Cited

U.S. PATENT DOCUMENTS

| 4,587,044 | A | 5/1986 | Miller et al. |
|---|---|---|---|
| 4,605,735 | A | 8/1986 | Miyoshi et al. |
| 4,667,025 | A | 5/1987 | Miyoshi et al. |
| 4,762,779 | A | 8/1988 | Snitman |
| 4,789,737 | A | 12/1988 | Miyoshi et al. |
| 4,824,941 | A | 4/1989 | Gordon et al. |
| 4,828,979 | A | 5/1989 | Klevan et al. |
| 4,835,263 | A | 5/1989 | Nguyen et al. |
| 4,876,335 | A | 10/1989 | Yamane et al. |
| 4,904,582 | A | 2/1990 | Tullis |
| 4,948,882 | A | 8/1990 | Ruth |
| 4,958,013 | A | 9/1990 | Letsinger |
| 5,013,830 | A | 5/1991 | Ohtsuka et al. |
| 5,082,830 | A | 1/1992 | Brakel et al. |
| 5,109,124 | A | 4/1992 | Ramachandran et al. |
| 5,112,963 | A | 5/1992 | Pieles et al. |
| 5,118,802 | A | 6/1992 | Smith et al. |
| 5,138,045 | A | 8/1992 | Cook et al. |
| 5,149,797 | A | 9/1992 | Pederson et al. |
| 5,214,136 | A | 5/1993 | Lin et al. |
| 5,218,105 | A | 6/1993 | Cook et al. |
| 5,220,007 | A | 6/1993 | Pederson et al. |
| 5,245,022 | A | 9/1993 | Weis et al. |
| 5,254,469 | A | 10/1993 | Warren, III et al. |
| 5,256,775 | A | 10/1993 | Froehler |
| 5,258,506 | A | 11/1993 | Urdea et al. |
| 5,262,536 | A | 11/1993 | Hobbs, Jr. |
| 5,272,250 | A | 12/1993 | Spielvogel et al. |
| 5,292,873 | A | 3/1994 | Rokita et al. |
| 5,317,098 | A | 5/1994 | Shizuya et al. |
| 5,366,878 | A | 11/1994 | Pederson |
| 5,371,241 | A | 12/1994 | Brush |
| 5,391,723 | A | 2/1995 | Priest |
| 5,403,711 | A | 4/1995 | Walder et al. |

(Continued)

FOREIGN PATENT DOCUMENTS

EP 2 502 997 A1 9/2012
WO 2003/093441 A2 11/2003

(Continued)

OTHER PUBLICATIONS

Sullivan et al. (2005) "SV40-encoded microRNAs regulate viral gene expression and reduce susceptibility to cytotoxic T cells," Nat. 435:682-686.
Svinarchuk et al. (1993) "Inhibition of HIV proliferation in MT-4 cells by antisense oligonucleotide conjugated to lipophilic groups," Biochimie. 75:49-54.
Vorobjev et al. (2001) Antisense Nucleic Acid Drug Dev. 11(2):77-85.
Weiler et al. (2006) "Anti-miRNA oligonucleotides (AMOs): ammunition to target miRNAs implicated in human disease?" Gene Ther. 13:496-502.
Zeng et al. (2003) "MicroRNAs and small interfering RNAs can inhibit mRNA expression by similar mechanisms," Proc. Natl. Acad. Sci. USA. 100:9779-9784.

(Continued)

Primary Examiner — Dana H Shin
(74) Attorney, Agent, or Firm — Lathrop GPM LLP; James H. Velema, Esq.; Michael Spellberg, Esq.

(57) ABSTRACT

The instant disclosure provides RNA-modulating agents that function to recruit one or more small regulatory RNA molecules (e.g., miRNA molecules, Y RNAs, and siRNAs) to a target mRNA thereby modulating (e.g., inhibiting) the translation of the target mRNA or destabilizing the mRNA. Also provided are miRNA inhibitors and diagnostic agents that have improved binding affinity for their target miRNAs. Methods for using the RNA-modulating agents, miRNA inhibitors and diagnostic agents are also provided.

11 Claims, 29 Drawing Sheets
Specification includes a Sequence Listing.

(56) References Cited

U.S. PATENT DOCUMENTS

| | | | |
|---|---|---|---|
| 5,414,077 A | 5/1995 | Lin et al. |
| 5,416,203 A | 5/1995 | Letsinger |
| 5,451,463 A | 9/1995 | Nelson et al. |
| 5,486,603 A | 1/1996 | Buhr |
| 5,491,133 A | 2/1996 | Walder et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness |
| 5,525,465 A | 6/1996 | Haralambidis et al. |
| 5,541,313 A | 7/1996 | Ruth |
| 5,545,730 A | 8/1996 | Urdea et al. |
| 5,552,538 A | 9/1996 | Urdea et al. |
| 5,565,350 A | 10/1996 | Kmiec |
| 5,565,552 A | 10/1996 | Magda et al. |
| 5,567,810 A | 10/1996 | Weis et al. |
| 5,574,142 A | 11/1996 | Meyer, Jr. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. |
| 5,587,371 A | 12/1996 | Sessler et al. |
| 5,591,584 A | 1/1997 | Chang et al. |
| 5,595,726 A | 1/1997 | Magda et al. |
| 5,597,696 A | 1/1997 | Linn et al. |
| 5,599,923 A | 2/1997 | Sessler et al. |
| 5,599,928 A | 2/1997 | Hemmi et al. |
| 5,608,046 A | 3/1997 | Cook et al. |
| 5,623,065 A | 4/1997 | Cook et al. |
| 5,652,355 A | 7/1997 | Metelev et al. |
| 5,652,356 A | 7/1997 | Agrawal |
| 5,683,874 A | 11/1997 | Kool |
| 5,684,143 A | 11/1997 | Gryaznov et al. |
| 5,688,941 A | 11/1997 | Cook et al. |
| 5,700,922 A | 12/1997 | Cook |
| 5,801,154 A | 9/1998 | Baracchini et al. |
| 7,307,067 B2 | 12/2007 | Sarnow et al. |
| 2001/0007902 A1 | 7/2001 | Silverman et al. |
| 2002/0187931 A1 | 12/2002 | Hayden et al. |
| 2003/0125241 A1 | 7/2003 | Wissenbach et al. |
| 2005/0221490 A1 | 10/2005 | Tuschl et al. |
| 2005/0256072 A1 | 11/2005 | Aronin et al. |
| 2006/0293267 A1 | 12/2006 | Zamore et al. |
| 2015/0299695 A1 | 10/2015 | Uhlmann et al. |

FOREIGN PATENT DOCUMENTS

| | | | |
|---|---|---|---|
| WO | 2004/009779 A2 | 1/2004 |
| WO | 2005/078096 A2 | 8/2005 |
| WO | 2005/097205 A2 | 10/2005 |
| WO | 2005/116250 A2 | 12/2005 |
| WO | 2006/113431 A2 | 10/2006 |
| WO | 2014/106837 A2 | 7/2014 |

OTHER PUBLICATIONS

International Search Report with Written Opinion corresponding to International Patent Application No. PCT/US2005/004206, dated Oct. 24, 2005.
International Search Report with Written Opinion corresponding to International Patent Application No. PCT/US2006/014059, dated May 25, 2007.
International Search Report with Written Opinion corresponding to International Patent Application No. PCT/US2015/052328, dated Feb. 8, 2016.
Broderick (2011) "Argonaute protein identity and pairing geometry determine cooperative in mammalian RNA silencing," RNA, 17:1858-1869.
Filipowicz et al., "Mechanisms of post-transcriptional regulation by micro RNAs: are the answers in sight?", Nature Reviews Genetics, vol. 9, pp. 102-114, Feb. 2008.
Doench et al., "Specificity of microRNA target selection in translational repression", Genes & Development, vol. 18, pp. 504-511, 2004.
Kawamata et al., "Structural determinants of miRNAs for RISC loading and slicer-independent unwinding", Nature Structural & Molecular Biology, vol. 16, No. 9, pp. 953-961, Sep. 2009.
Jopling et al., "Position-dependent function for a tandem microRNA miR-122-binding site located in the hepatitis C virus RNA genome", Cell Host & Microbe, vol. 4, pp. 77-85, Jul. 17, 2008.
Lewis et al., "Conserved seed pairing, often flanked by adenosines, indicates that thousands of human genes are microRNA targets", Cell, vol. 120, pp. 15-20, Jan. 14, 2005.
Akbergenov et al. (2006) "Molecular characterization of geminivirus-derived small RNAs in different plant species," Nucleic Acids Res. 34(2):462-471.
Bennasser et al. (2004) "HIV-1 encoded candidate micro-RNAs and their cellular targets," Retrovirology. 1:43. pp. 1-5.
Boulta et al. (2003) "Developmental defects by antisense-mediated inactivation of micro-RNAs 2 and 13 in *Drosophila* and the identification of putative target genes," Nucleic Acids Res. 31:4973-4980.
Braasch et al. (2003) "RNA Interference in Mammalian Cells by Chemically-Modified RNA," Biochem. 42:7967-7975.
Cai et al. (2005) "Kaposi's sarcoma-associated herpesvirus expresses an array of viral microRNAs in latently infected cells," Proc. Natl. Acad. Sci. USA. 102(15):5570-5575.
Cai et al. (2006) "Transcriptional Origin of Kaposi's Sarcoma-Associated Herpesvirus MicroRNAs," Journal of Virology. 80(5):2234-2242.
Cai et al. (2006) "Epstein-Barr Virus MicroRNAs Are Evolutionarily Conserved and Differentially Expressed," PloS Pathogens. 2(3):e23 pp. 0236-0247.
Crooke (2001) "Basic Priciples of Antisense Technology," Ch.1 In; Antisense Drug Technology. Springer-Verlag. pp. 1-28.
Crooke et al. (1996) "Pharmacokinetic properties of several novel oligonucleotide analogs in mice," J. Pharmacol. Exp. Ther. 277:923-937.
Doench et al. (2003) "siRNAs can function as miRNAs," Genes Dev. 17:438-442.
Dunn et al. (2005) "Human cytomegalovirus expresses novel microRNAs during productive viral infection," Cell. Microbiol. 7(11):1684-1695.
Duykxhoorn et al. (2003) "Killing the messenger: short RNAs that silence gene expression," Nat. Rev. Mol. Cell. Biol. 4:457-467.
Ebert et al. (2007) "MicroRNA sponges: competitive inhibitors of small RNAs in mammalian cells", Nat. Methods. 4 (9):721-726.
Eckstein (2000) "Phosphorothioate Oligodeoxynucleotides: What Is Their Origin and What Is Unique About Them?" Antisense Nucleic Acid Drug Dev. 10(2):117-121.
Griffiths-Jones (2004) "The microRNA registry," Nucleic Acids Res. 32(Database Issue):D109-D111.
Grundhoff et al. (2006) "A combined computational and microarray-based approach identifies novel microRNAs encoded by human gamma-herpesviruses," RNA. 12:733-750.
Hutvagner et al. (2001) "A Cellular Function for the RNA-Interference Enzyme Dicer in the Maturation of the let-7 Small Temporal RNA," Science. 293:834-838.
Hutvagner et al. (2002) "A microRNA in a multiple-turnover RNAi enzyme complex," Science. 297:2056-2060.
Hutvagner et al. (2004) "Sequence-Specific Inhibition of Small RNA Function," PloS Biology. 2(4):0465-0475.
Jen et al. (2000) "Suppression of Gene Expression by Targeted Disruption of Messenger RNA: Available Options and Current Strategies," Stem Cells. 18:307-319.
Kabanov et al. (1990) "A new class of antivirals: antisense oligonucleotides combined with a hydrophobic substituent effectively inhibit influenza virus reproduction and synthesis of virus-specific proteins in MDCK cells," FEBS Lett. 259:327-330.
Khvorova et al. (2003) "Functional siRNAs and miRNAs exhibit strand bias," Cell. 115(2):209-216.
Krichevsky et al. (2003) "A microRNA array reveals extensive regulation of microRNAs during brain development," RNA 9:1274-1281.

(56) References Cited

OTHER PUBLICATIONS

Lagos-Quintana et al. (2001) "Identification of novel genes coding for small expressed RNAs," Science. 294 (5543):853-858.
Lagos-Quintana et al. (2002) "Identification of tissue-specific microRNAs from mouse," Current Biol. 12:735-739.
Lau et al. (2001) "An abundant class of tiny RNAs with probable regulatory roles in Caenorhabditis elegans," Science. 294:858-862.
Lee et al. (2001) "An extensive class of small RNAs in Caenorhabditis elegans," Science. 294:862-864.
Letsinger et al. (1989) "Cholesteryl-conjugated oligonucleotides: synthesis, properties, and activity as inhibitors of replication of human immunodeficiency virus in cell culture," Proc. Natl. Acad. Sci. USA. 86:6553-6556.
Lim et al. (2003) "Vertebrate microRNA genes," Science. 299:1540.
Lu et al. (2005) "Delivering siRNA in vivo for functional genomics and novel therapeutics," Ch. 22 In; RNA Interference Technology. Ed: Appasani. Cambridge University Press, pp. 303-317.
Manoharan et al. (1992) "Chemical modifications to improve uptake and bioavailability of antisense oligonucleotides," Ann. N.Y. Acad. Sci. 660:306-309.
Manoharan et al. (1993) "Introduction of a lipophilic thioether tether in the minor groove of nucleic acids for antisense applications," Bioorgan. Med. Chem. Lett. 3:2765-2770.
Manoharan et al. (1994) "Cholic acid-oligonucleotide conjugates for antisense applications," Bioorgan. Med. Chem. Lett. 4:1053-1060.
Manoharan et al. (1995) "Oligonucleotide Conjugates: Alteration of the Pharmacokinetic Properties of Antisense Agents," Nucleosides and Nucleotides. 14:969-973.
Manoharan et al. (1995) "Lipidic nucleic acids," Tetrahedron Letters. 36:3651-3654.
Matsuda et al. (Mar. 2, 2015) "siRNA Conjugates Carrying Sequentially Assembled Trivalent N-Acetylgalactosamine Linked Through Nucleosides Elicit Robust Gene Silencing In Vivo in Hepatocytes," ACS Chem. Biol. 10:1181-1187.
Mishra et al. (1995) "Improved leishmanicidal effect of phosphorotioate antisense oligonucleotides by LDL-mediated delivery," Biochim. Biophys. Acta. 1264:229-237.

Nair et al. (2006) "Virus-encoded microRNAs: novel regulators of gene expression," Trends in Microbiology. 14 (4):169-175.
Oberhauser et al. (1992) "Effective incorporation of 2'-O-methyl-oligoribonucleotides into liposomes and enhanced cell association through modification with thiocholesterol," Nucleic Acids Res. 20:533-538.
Pasquinelli et al. (2000) "Conservation of the sequence and temporal expression of let-7 heterochronic regulatory RNA," Nat. 408:86-89.
Perreault (2007) "Ro-associated Y RNAs in metazoans: evolution and diversification," Mol. Biol. Evol. 24(8):1678-1689.
Petersen et al. (2003) "LNA: a versatile tool for therapeutics and genomics," Trends Biotechnol. 21:74-81.
Pfeffer et al. (2004) "Identification of virus-encoded microRNAs," Science. 304:734-736.
Prakash et al. (Jul. 2014) "Targeted delivery of antisense oligonucleotides to hepatocytes using triantennary N-acetyl galactosamine improves potency 10-fold in mice," Nucleic Acids Res. 42(13):8796-8807.
Rusckowski et al. (2000) "Biodistribution and metabolism of a mixed backbone oligonucleotide (GEM 231) following single and multiple dose administration in mice," Antisense Nucleic Acid Drug Dev. 10(5):333-345.
Samols et al. (2005) "Cloning and identification of a microRNA cluster within the latency-associated region of Kaposi's sarcoma-associated herpesvirus," Journal of Virology. 79(14):9301-9305.
Sano et al. (2006) "Sequence-specific interference by small RNAs derived from adenovirus VAI RNA," FEBS Lett. 580:1553-1564.
Schwarz et al. (2003) "Asymmetry in the assembly of the RNAi enzyme complex," Cell. 115:199-208.
Shea et al. (1990) "Synthesis, hybridization properties and antiviral activity of lipid-oligodeoxynucleotide conjugates," Nucleic Acids Res. 18:3777-3783.
Stein et al. (2000) "Inhibition of Vesivirus infections in mammalian tissue culture with antisense morpholino oligomers," Antisense Nucleic Acid Drug Dev. 11(5):317-325.
Rusk, "When microRNAs activate translation", Nature Methods, Feb. 2008, 5(2): 122-123.
Zhang et al., "MicroRNA Directly Enhances Mitochondrial Translation during Muscle Differentiation", Cell, Jul. 31, 2014, 158(3): 607-619.

```
                              8   5   2
miR-1    3'-UAU GUA UGA AGA AAU GUA AGG U-5' SEQ ID NO:1
miR-122  3'-GUU UGU GGU AAC AGU GUG AGG U-5' SEQ ID NO:2
                              seed
``` miR-122 pairing miR-1 tether:

```
                       8   5   2
3'-GUU UGU GGU AAC AGU GUG AGG U-5' SEQ ID NO:2
5'-AUA CAU ACU UCU UUA CAU UCC A ccguguuagcuuug-3'
                                    SEQ ID NO:3
``` miR-122 pairing miR-122 tether:

```
3'-GUU UGU GGU AAC AGU GUG AGG U-5' SEQ ID NO:2
5'-CAA ACA CCA UUG UCA CAC UCC A ccguguuagcuuug-3'
                                    SEQ ID NO:4
```

*Fig. 6B* perfect pairing            bulged p10-11 pairing perfect pairing $IC_{50} = 0.08 \pm 0.02$ nM
$n^H = 1.1 \pm 0.14$ bulged p10-11 pairing $IC_{50} = 0.008 \pm 0.001$ nM
$n^H = 0.99 \pm 0.08$ $IC_{50} = 0.07 \pm 0.07$ nM
$n^H = 0.96 \pm 0.59$ $IC_{50} = 0.23 \pm 0.06$ nM
$n^H = 1.1 \pm 0.3$ 1xmiR-122 perfect
$IC_{50} = 0.07 \pm 0.07$ nM 1xmiR-122 bulged
$IC_{50} = 0.23 \pm 0.06$ nM 2xmiR-122 perfect
$IC_{50} = 0.08 \pm 0.02$ nM 2xmiR-122 bulged
$IC_{50} = 0.008 \pm 0.001$ nM perfect pairing | bulged p10-11 pairing seed p2-8 pairing | seed p2-8, T9A pairing ·······△······· 2xmiR-122 perfect
$IC_{50}$ = 0.08 ± 0.02 nM – –○– – 2xmiR-122 p10-11 bulged
$IC_{50}$ = 0.008 ± 0.001 nM ·······△······· T536 2xperfect miR122 n=9
– –○– – T542 2xmiR122 p10-11 n=18 perfect pairing

$IC_{50} = 0.08 \pm 0.02$ nM
$n^H = 1.1 \pm 0.14$ bulged p10-11 pairing

$IC_{50} = 0.008 \pm 0.001$ nM
$n^H = 0.99 \pm 0.08$ seed p2-8 pairing

$IC_{50} = 0.66 \pm 0.24$ nM
$n^H = 1.1 \pm 0.5$ seed p2-8, T9A pairing

$IC_{50} = 0.13 \pm 0.03$ nM
$n^H = 1.3 \pm 0.3$ perfect pairing

59 nt

$IC_{50} = 0.08 \pm 0.02$ nM
$n^H = 1.1 \pm 0.14$ bulged p10-11 pairing

59 nt

$IC_{50} = 0.008 \pm 0.001$ nM
$n^H = 0.99 \pm 0.08$ seed p2-8 pairing

31 nt

$IC_{50} = 0.66 \pm 0.24$ nM
$n^H = 1.1 \pm 0.5$ seed p2-8, T9A pairing

33 nt

$IC_{50} = 0.13 \pm 0.03$ nM
$n^H = 1.3 \pm 0.3$

Fig. 14C t9A p10-11mm, p12-16 paired

T559

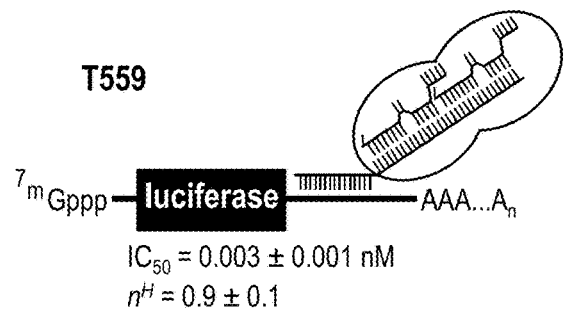

$IC_{50} = 0.003 \pm 0.001$ nM
$n^H = 0.9 \pm 0.1$ t9A p10-11mm, p12-17 paired

T560

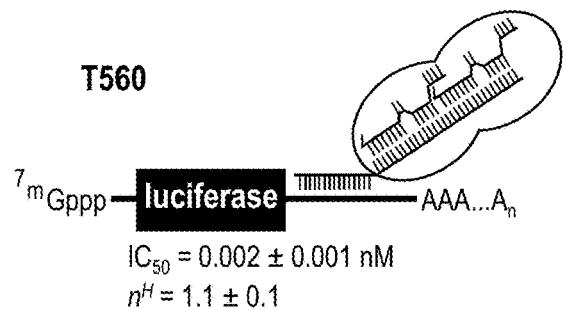

$IC_{50} = 0.002 \pm 0.001$ nM
$n^H = 1.1 \pm 0.1$

**Supplemental 3' pairing of T2xmiR-122 T9A, p10-11mm
pAAV Cyp Gaussia 6xCXCR4 8-4-14 n=12(rep1, 2, 3 and high IC50)**

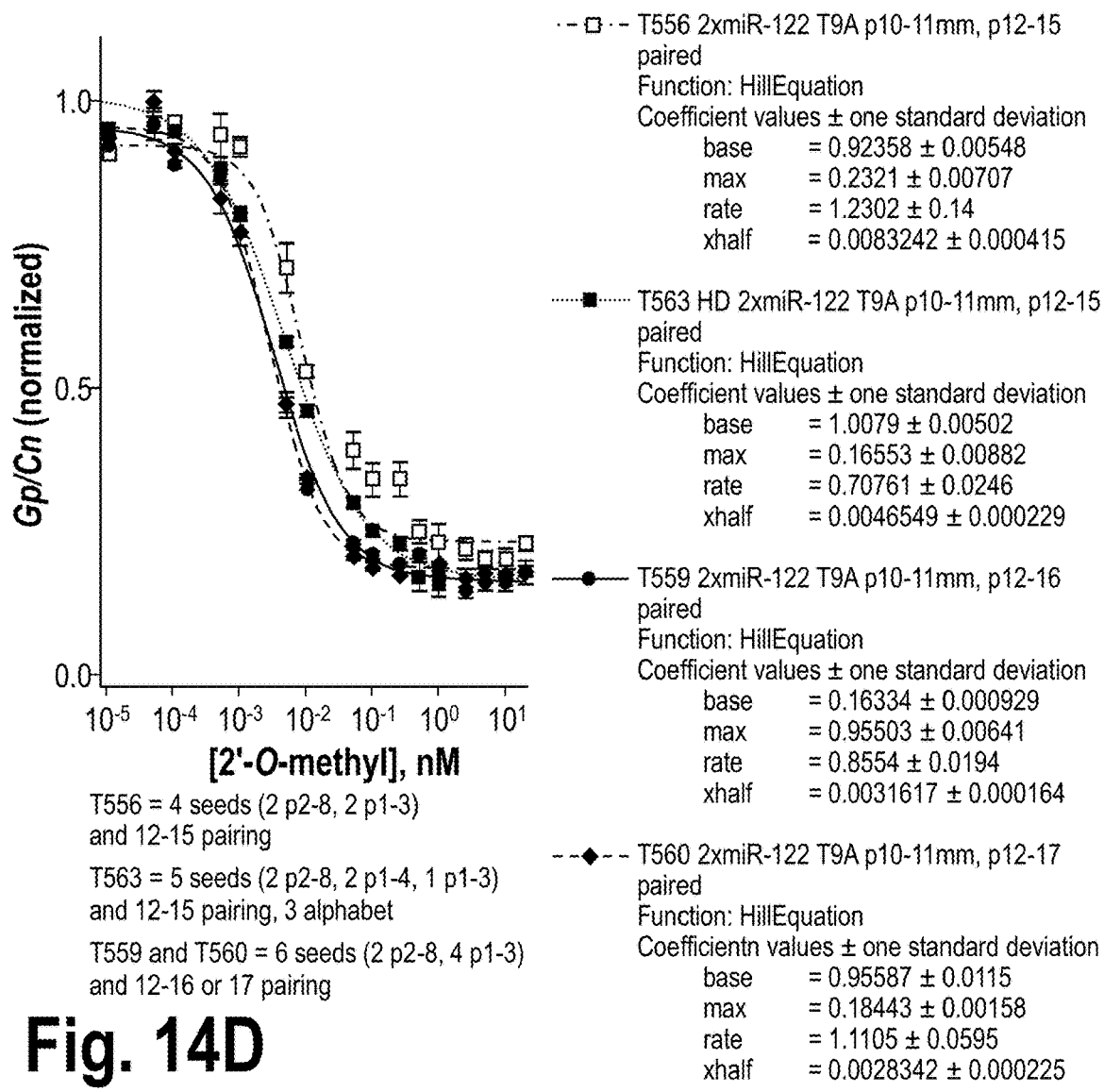

- -□- - T556 2xmiR-122 T9A p10-11mm, p12-15 paired
  Function: HillEquation
  Coefficient values ± one standard deviation
  base  = 0.92358 ± 0.00548
  max   = 0.2321 ± 0.00707
  rate  = 1.2302 ± 0.14
  xhalf = 0.0083242 ± 0.000415

- ····■···· T563 HD 2xmiR-122 T9A p10-11mm, p12-15 paired
  Function: HillEquation
  Coefficient values ± one standard deviation
  base  = 1.0079 ± 0.00502
  max   = 0.16553 ± 0.00882
  rate  = 0.70761 ± 0.0246
  xhalf = 0.0046549 ± 0.000229

- ——●—— T559 2xmiR-122 T9A p10-11mm, p12-16 paired
  Function: HillEquation
  Coefficient values ± one standard deviation
  base  = 0.16334 ± 0.000929
  max   = 0.95503 ± 0.00641
  rate  = 0.8554 ± 0.0194
  xhalf = 0.0031617 ± 0.000164

- --◆-- T560 2xmiR-122 T9A p10-11mm, p12-17 paired
  Function: HillEquation
  Coefficientn values ± one standard deviation
  base  = 0.95587 ± 0.0115
  max   = 0.18443 ± 0.00158
  rate  = 1.1105 ± 0.0595
  xhalf = 0.0028342 ± 0.000225

T556 = 4 seeds (2 p2-8, 2 p1-3) and 12-15 pairing

T563 = 5 seeds (2 p2-8, 2 p1-4, 1 p1-3) and 12-15 pairing, 3 alphabet

T559 and T560 = 6 seeds (2 p2-8, 4 p1-3) and 12-16 or 17 pairing

Fig. 14D

3/25/14    3 weeks post infection

RLU Cypridina luciferase

| pAAV 6xCXCR4 Injection mouse eartag number | 1x10^12 dose | | | 1x10^11 dose | | | 1x10^10 dose | | | PBS | PBS | positive control Huh7.5 cells |
|---|---|---|---|---|---|---|---|---|---|---|---|---|
| | 8988 | 8989 | 8990 | 8985 | 8986 | 8987 | 8982 | 8983 | 8984 | 9201 | 9202 | |
| 10 uL of 1:100 dil H20 | 12041799 | 33921020 | 24456550 | 13342349 | 9228577 | 12897423 | 3498279 | 3180347 | 3515898 | 200 | 1965 | 3323489 |
| 10 uL of 1:100 dil H20 | 11205315 | 31811204 | 22807972 | 12791992 | 9120952 | 12921489 | 3479051 | 3189178 | 3571371 | 175 | 1930 | |
| 10 uL of 1:100 dil H20 | 11805716 | 32931898 | 22941282 | 13087742 | 9212701 | 13091001 | 3519351 | 3165829 | 3474115 | 196 | 1819 | |
| TTEST | | 0.0003 | 0.0010 | | 0.0011 | 0.6111 | | 0.0033 | 0.6419 | | | |
| TTEST | | | 0.0009 | | 0.0003 | | | 0.0040 | | | | |

RLU Gaussia luciferase

| pAAV 6xCXCR4 Injection mouse eartag number | 1x10^12 dose | | | 1x10^11 dose | | | 1x10^10 dose | | | PBS | PBS | positive control Huh7.5 cells |
|---|---|---|---|---|---|---|---|---|---|---|---|---|
| | 8988 | 8989 | 8990 | 8985 | 8986 | 8987 | 8982 | 8983 | 8984 | 9201 | 9202 | |
| 10 uL of 1:100 dil H20 | 646417 | 932545 | 671125 | 334180 | 175325 | 196829 | 46233 | 48173 | 35886 | 441 | 473 | 791541 |
| 10 uL of 1:100 dil H20 | 657527 | 804665 | 673133 | 238307 | 160618 | 184759 | 37845 | 34626 | 31061 | 392 | 446 | |
| 10 uL of 1:100 dil H20 | 554293 | 627849 | 680716 | 190136 | 152873 | 142485 | 31895 | 29856 | 30421 | 501 | 658 | |
| TTEST | | 0.1134 | 0.2581 | | 0.1253 | 0.1110 | | 0.5520 | 0.1379 | | | |
| TTEST | | 0.3397 | | | 0.4006 | | | 0.3108 | | | | |
| Gp/Cn | 0.054 | 0.027 | 0.027 | 0.025 | 0.019 | 0.015 | 0.013 | 0.015 | 0.010 | | | |
| Gp/Cn | 0.059 | 0.025 | 0.030 | 0.019 | 0.018 | 0.014 | 0.011 | 0.011 | 0.009 | | | |
| Gp/Cn | 0.047 | 0.019 | 0.030 | 0.015 | 0.017 | 0.011 | 0.009 | 0.009 | 0.009 | | | |
| Gp/Cn AVE | 0.053 | 0.024 | 0.029 | 0.019 | 0.018 | 0.013 | 0.011 | 0.012 | 0.009 | | | 0.24 |
| STDEV | 0.0048 | 0.0038 | 0.0010 | 0.0043 | 0.0010 | 0.0019 | 0.0017 | 0.0024 | 0.0007 | | | |
| TTEST | | 0.0055 | 0.0211 | | 0.5538 | 0.0929 | | 0.3309 | 0.1490 | | | |
| TTEST | | 0.2527 | | | 0.0289 | | | 0.1739 | | | | |

| T567 | mC.mC.mA.mU.mU.mC.mA.mA.mG.mA.mA.mG.mC.mU.mU.mC.mC.mU.mU.mA.mG.mA.mA.mG.mA.mA.mA.mC. SEQ ID NO:5 |
|---|---|
| | mC.mC.mC.mA.mA.mU.mU.mG.mA.mA.mU.mG.mU.mU.mG.mC.mA.mA.mG.mA.mA.mG.mA.mA.mA.mG.mA.mA.mC. |
| | 12-16 paired |
| T568 | mA.mC.mC.mA.mA.mU.mU.mG.mA.mA.mU.mG.mU.mU.mG.mC.mA.mA.mG.mA.mA.mG.mA.mA.mG.mA.mA.mA.mC. SEQ ID NO:6 |
| | mC.mC.mU.mC.mA.mA.mA.mG.mC.mU.mG.mC.mU.mC.mA.mC.mU.mC.mA.mA.mG.mA.mA.mG.mA.mG.mC.mU.mC.mA.mC.mC SEQ ID NO:6 |
| | 12-17 paired |

Fig. 18B

Huh7.5 cells 48h post-transfection
tether to miR-122
qRT-PCR APOC3

| 2x seed plus: | Tether number | [tether] | 8/29/2014 2-ddC(T) | 9/1/2014 2-ddC(T) | 9/11/2014 2-ddC(T) | AVE 2-ddC(t) | STDEV | STDERROR |
|---|---|---|---|---|---|---|---|---|
| 12-16 paired | T567 | 10 nM | 0.69 | 0.31 | 0.48 | 0.49 | 0.15 | 0.09 |
| 12-16 paired | T567 | 25 nM | 0.68 | 0.46 | 0.56 | 0.57 | 0.09 | 0.05 |
| 12-16 paired | T567 | 50 nM | 0.53 | 0.46 | 0.51 | 0.50 | 0.03 | 0.02 |
| 12-16 paired | T567 | 75 nM | 0.64 | 0.39 | 0.56 | 0.53 | 0.11 | 0.06 |
| 12-16 paired | T567 | 100 nM | 0.58 | 0.51 | 0.73 | 0.61 | 0.09 | 0.05 |
| 12-16 paired | T567 | 150 nM | 0.70 | 0.52 | 0.63 | 0.62 | 0.08 | 0.04 |
| 12-17 paired | T568 | 10 nM | 0.73 | 0.52 | 0.37 | 0.54 | 0.14 | 0.08 |
| 12-17 paired | T568 | 25 nM | 0.59 | 0.44 | 0.51 | 0.52 | 0.06 | 0.03 |
| 12-17 paired | T568 | 50 nM | 0.49 | 0.47 | 0.46 | 0.47 | 0.01 | 0.01 |
| 12-17 paired | T568 | 75 nM | 0.60 | 0.58 | 0.48 | 0.55 | 0.05 | 0.03 |
| 12-17 paired | T568 | 100 nM | 0.55 | 0.50 | 0.61 | 0.55 | 0.04 | 0.02 |
| 12-17 paired | T568 | 150 nM | 0.63 | 0.51 | 0.69 | 0.61 | 0.08 | 0.04 |

ApoC-III at 3 days post injection

** p-value = 0.003 compared to PBS (Bonferroni)
** p-value = 0.004 compared to PBS
*** p-value = 0.0006 compared to PBS
**** p-value < 0.0001 compared to PBS Triclycerides at 3 days post injection

* indicates p-value = 0.03 compared to PBS (Bonferroni)
** indicates p-value = 0.008 compared to PBS

T567 = miR-122/ ApoC-III tether recruits miR-122 RISC to a single
15 nt site in 3' UTR of ApoC-III

T559 = miR-122/ CXCR4 control for miR-122 inhibition
tether binds miR-122,
but cannot bind ApoC-III

T571 = miR166/ ApoC-III control for antisense
tether binds ApoC-III,
but does not recruit miRISC

RNA-MODULATING AGENTS

RELATED APPLICATIONS

This application is a continuation of U.S. patent application Ser. No. 14/866,186, filed Sep. 25, 2015, which claims priority to U.S. Provisional Application No. 62/055,759, filed Sep. 26, 2014, the entire contents of which are incorporated herein by reference.

STATEMENT OF FEDERALLY SPONSORED RESEARCH

This invention was made with Government support under Grant No. TR000161 awarded by the National Institutes of Health. The Government has certain rights in the invention.

BACKGROUND

Small interfering RNAs (siRNAs) and microRNAs (miRNAs) repress gene expression through nucleic acid base-pairing between the target mRNA and the small RNA guide bound to a member of the Argonaute family of proteins. The use of siRNAs and miRNAs to treat diseases and viral infections of non-hepatic origin requires designing siRNAs and miRNAs that effectively trigger gene silencing in vivo, resist nucleolytic degradation, and accumulate in the correct tissue and cell type. Presently, no current delivery strategy can effectively and selectively silence disease-causing or viral genes in some tissues but not others.

Accordingly, there is a need in the art for novel compositions for mediating gene silencing that can be administered systemically, but yet can act in a tissue specific manner.

SUMMARY

The instant disclosure provides RNA-modulating agents that function to recruit one or more small regulatory RNA molecules (e.g., miRNA molecules, Y RNAs, and siRNAs) to a target mRNA thereby modulating (e.g., inhibiting) the translation of the target mRNA or destabilizing the mRNA. Also provided are miRNA inhibitors and diagnostic agents that have improved binding affinity for their target miRNAs. Methods for using the RNA-modulating agents, miRNA inhibitors and diagnostic agents are also provided.

The instant disclosure is based on the surprising discovery that RNA-modulating agents comprising two or more miRNA binding sequences are significantly more potent at inhibiting translation from target mRNA or destabilizing the mRNA than RNA-modulating agents having a single miRNA binding sequence. Furthermore, Applicants demonstrate herein that the potency of an RNA-modulating agent comprising two or more miRNA binding sequences can be further improved (e.g., over 10-fold) by employing miRNA binding sequences that have specific combinations of Watson-Crick base pairs and mismatches with their cognate miRNA binding partner. While not wishing to be bound by theory, Applicants believe that the improved potency of the RNA-modulating agents disclosed herein is, in part, facilitated by enhanced binding of Argonaute proteins by the RNA-modulating agent.

The RNA-modulating agents disclosed herein have a number of advantageous features. For example, these RNA-modulating agents can modulate (e.g., silence) gene expression using desired endogenous miRNAs, even though the target mRNA does not possess a binding site for that miRNA. Accordingly, the disclosed RNA-modulating agents can be used to target any gene in a cell or organism, including viral genes. The disclosed RNA-modulating agents also allow for cell type-specific or tissue-specific gene modulation (e.g., silencing) by recruitment of miRNA that are cell type-specific or tissue-specific (e.g., miR-122 which is liver-specific, and miR-1 which is muscle-specific).

The miRNA inhibitors and diagnostic agents disclosed herein employ miRNA binding sequences with enhanced miRNA-binding characteristics that improve the potency of the miRNA inhibitors and improve the sensitivity of the diagnostic agents.

Accordingly, in one aspect the instant disclosure provides an RNA-modulating agent comprising an mRNA binding sequence that is complementary to a portion of a target mRNA sequence, linked to two or more miRNA binding sequences, wherein one or more of the miRNA binding sequences are complementary to at least positions 2 to 8 of an miRNA, but not complementary to positions 10 and 11 of the miRNA.

In certain embodiments, the miRNA binding sequences are complementary to positions 2 to 8, and at least 12 to 25 of the miRNA (e.g., 12-15, 12-16, 12-17, 12-18, 12-19, 12-20, 12-21, 12-22, 12-23, 12-24, or 12-25) but not complementary to positions 10 and 11 of the miRNA. In certain embodiments, the miRNA binding sequences are not complementary to position 1 of the miRNA. In certain embodiments, the miRNA binding sequences are complementary to positions 2 to 8, and at least 12 to 25 of the miRNA (e.g., 12-15, 12-16, 12-17, 12-18, 12-19, 12-20, 12-21, 12-22, 12-23, 12-24, or 12-25), but not complementary to positions 1, 10 and 11 of the miRNA. In certain embodiments, one or more of the miRNA binding sequences are complementary to only positions 2 to 8 of the miRNA. In certain embodiments, one or more of the miRNA binding sequences have an adenosine, at a position in the miRNA binding sequence corresponding to position 9 of the miRNA.

In certain embodiments, the miRNA binding sequences are complementary to positions 2 to 8, and at least 12 to 16 of the miRNA (e.g., 12-15 or 12-16) but not complementary to positions 10 and 11 of the miRNA. In certain embodiments, the miRNA binding sequences are not complementary to position 1 of the miRNA. In certain embodiments, the miRNA binding sequences are complementary to positions 2 to 8, and at least 12 to 16 of the miRNA (e.g., 12-15 or 12-16), but not complementary to positions 1, 10 and 11 of the miRNA. In certain embodiments, one or more of the miRNA binding sequences are complementary to only positions 2 to 8 of the miRNA. In certain embodiments, one or more of the miRNA binding sequences have an adenosine, at a position in the miRNA binding sequence corresponding to position 9 of the miRNA. In certain embodiments, the miRNA binding sequences are not complementary to at least one position selected from positions 17 to 22 of the miRNA (e.g., one, two, three, four, five or six positions selected from positions 17 to 22 of the miRNA). In certain embodiments, the miRNA binding sequences are not complementary to positions 17 to 22 of the miRNA.

In certain embodiments, the miRNA binding sequences described herein form one or more bulged structures when bound to the miRNA. In certain embodiments, the bulged structure is a single unpaired nucleotidyl residue only within the miRNA binding sequences. In certain embodiments, the unpaired nucleotidyl residue is a guanosine. In certain embodiments, the miRNA binding sequences are not complementary to positions 9 and 10 of the miRNA. In certain embodiments, the miRNA binding sequences are not complementary to positions 9-11 of the miRNA. In certain embodiments, the miRNA binding sequences are not complementary to positions 9-12 of the miRNA. In certain embodiments, the miRNA binding sequences are not complementary to positions 9-13 of the miRNA. In certain embodiments, the miRNA binding sequences are not complementary to positions 9-14 of the miRNA. In certain embodiments, the miRNA binding sequences are not complementary to positions 9-15 of the miRNA. In certain embodiments, the miRNA binding sequences are not complementary to positions 9-16 of the miRNA. In certain embodiments, the miRNA binding sequences are complementary to positions 17-22 of the miRNA.

In certain embodiments, one or more of the miRNA binding sequences are about 8 to about 15 nucleotides in length. In certain embodiments, the mRNA binding sequence is about 15 nucleotides in length.

In certain embodiments, the RNA-modulating agent comprises two miRNA binding sequences. In certain embodiments, the RNA-modulating agent comprises three miRNA binding sequences. In certain embodiments, the miRNA binding sequences bind to the same miRNA.

In certain embodiments, the miRNA binding sequences are linked together in series in the RNA-modulating agent. In certain embodiments, the mRNA binding sequence is flanked by miRNA binding sequences in the RNA-modulating agent. In certain embodiments, the miRNA binding sequences are linked together in series, and linked to the 5' end of the mRNA binding sequence. In certain embodiments, the miRNA binding sequences are linked together in series, and linked to the 3' end of the mRNA binding sequence.

In certain embodiments, the miRNA is a tissue specific miRNA. In certain embodiments, the miRNA is a microRNA whose expression is increased in a diseased state, oncogenic transformation or during or to promote viral infection. In certain embodiments, the miRNA is selected form the group consisting of miR122, miR-1, let-7, miR-103, miR-107 miR-216, miR-375, miR-124, miR-125, miR-128, miR-132, miR-134, miR-135, miR-138, miR-153, miR-143, miR-194, miR-133a, miR-206, miR-208, miR-142-3p, miR-143-5p, miR-181, miR-195, miR-221, miR-222, miR-192, miR-194, miR-204, miR-215, miR-30b, miR-30c, miR-122a, miR-152, miR-199, miR-215,miR-130, miR-24, miR-32, miR-189, miR-127, miR-150, miR-151, miR-212, miR-148, miR-204, miR-378, and a viral microRNA.

In certain embodiments, the miRNA is an exogenous miRNA. In certain embodiments the exogenous miRNA is an artificial exogenous miRNA.

In certain embodiments, the target mRNA is a nuclear mRNA. In certain embodiments, the target mRNA is a cytoplasmic mRNA. In certain embodiments, the target mRNA is a mitochondrial mRNA. In certain embodiments, the target mRNA is a viral mRNA. In certain embodiments, the target mRNA encodes a protein that causes a disease or disorder. In certain embodiments, the target mRNA encodes a protein that is overexpressed or overactive. In certain embodiments, the target mRNA encodes a protein that is underexpressed or underactive. In certain embodiments, the target mRNA encodes a gene whose aberrant expression causes a diseased state, oncogenic transformation or promotes viral infection.

In certain embodiments, the target mRNA is APOC3, SOD1, a mitochondrial RNA, a viral RNA (an RNA from Hepatitis B virus (HBV), Hepatitis C virus (HCV), Ebola virus (EBOV), Marburg virus (MARV), Herpes simplex virus (HSV), Cytomegalovirus (CMV), Epstein-Barr virus (EBV), Eastern equine encephalitis virus (EEEV), Venezuelan equine encephalitis virus (VEEV).

In certain embodiments, the RNA-modulating agent is a polynucleotide. In certain embodiments, the RNA-modulating agent contains one or more modified nucleotides selected from the group consisting of a $N^6$-methyladenosine ($m^6A$), pseudouridine, 2'-deoxy-2'-fluoro modified nucleotide, a 2'-deoxy-modified nucleotide, a locked nucleotide (LNA), a C2'-O,C4'-ethylene-bridged nucleotide, an abasic nucleotide, 2'-fluoroarabino-modified nucleotide, 2'-amino-modified nucleotide, 2'-alkyl-modified nucleotide, morpholino nucleotide, a phosphoramidate, and a non-natural base comprising nucleotide, a 2'-O-methyl modified nucleotide, a 2'-O-methoxyethyl modified nucleotide, a nucleotide comprising a 5'-phosphorothioate group, and a terminal nucleotide linked to a cholesteryl derivative or dodecanoic acid bisdecylamide group.

In another aspect, the instant disclosure provides a method of modulating expression of a target protein in a cell, the method comprising delivering into the cytoplasm or nucleus of the cell an RNA-modulating agent, as disclosed herein, that binds to the mRNA encoding the target protein and modulates the translation of the target protein. In certain embodiments, the RNA-modulating agent decreases expression of a target protein. In certain embodiments, the RNA-modulating agent increases expression of a target protein. In certain embodiments, the cell is present in an organism (e.g., a plant or an animal).

In another aspect, the instant disclosure provides a method of treating a subject having a disease or disorder characterized by or caused by: (a) the overexpression or overactivity of a normal cellular protein; (b) the underexpression or underactivity of a normal cellular protein; (c) the activity of a mutant protein; or (d) the activity of a viral RNA or protein, the method comprising administering to the subject an effective amount of an RNA-modulating agent, as disclosed herein, wherein the RNA-modulating agent binds to the mRNA encoding the protein and modulates expression of a protein.

In another aspect, the instant disclosure provides an isolated miRNA binding sequence that is complementary to at least positions 2 to 8 of an miRNA, but not complementary to positions 10 and 11 of the miRNA. In certain embodiments, the miRNA binding sequence has one or more of the following properties: a) the miRNA binding sequence is complementary to positions 2 to 8, and at least 12 to 25 of the miRNA (e.g., 12-15, 12-16, 12-17, 12-18, 12-19, 12-20, 12-21, 12-22, 12-23, 12-24, or 12-25), but not complementary to positions 10 and 11 of the miRNA; b) the miRNA binding sequence is not complementary to position 1 of the miRNA; c) the miRNA binding sequences is complementary to positions 2 to 8, at least 12 to 25 of the miRNA (e.g., 12-15, 12-16, 12-17, 12-18, 12-19, 12-20, 12-21, 12-22, 12-23, 12-24, or 12-25), but not complementary to positions 1, 10 and 11 of the miRNA; d) the miRNA binding sequence is complementary to only positions 2 to 8 of the miRNA; e) the miRNA binding sequences has an adenosine, at a position in the miRNA binding sequence corresponding to position 9 of the miRNA; f) the miRNA binding sequences are about 8 to about 25 nucleotides in length.

In another aspect, the instant disclosure provides a diagnostic agent comprising two or more miRNA binding sequence disclosed herein linked to a detectable label. In certain embodiments the detectable label is a fluorescent molecule.

In another aspect, the instant disclosure provides an oligonucleotide array comprising a plurality of the diagnostic agents disclosed herein.

In another aspect, the instant disclosure provides an miRNA inhibitor comprising two or more miRNA binding sequence disclosed herein.

In another aspect, the instant disclosure provides a method of detecting an miRNA is a sample, the method comprising contacting the sample with a diagnostic agent or an array, as disclosed herein, and detecting the formation of a complex between the diagnostic agent or array and the miRNA, wherein the presence of a complex between the diagnostic agent or array and the miRNA is indicative of the presence of the miRNA in the sample. In certain embodiments, the sample is a body fluid, tissue, or cell.

In another aspect, the instant disclosure provides a method of inhibiting the activity of an miRNA in a cell, the method comprising delivering into the cell an miRNA inhibitor, as disclosed herein, that binds to the miRNA and inhibits activity of the miRNA. In certain embodiments, the cell is present in an organism.

In another aspect, the instant disclosure provides a method of treating a subject having a disease or disorder characterized by or caused by the activity of an miRNA, the method comprising the method comprising administering to the subject an effective amount of an miRNA inhibitor, as disclosed herein, that binds to the miRNA inhibits activity of the miRNA, thereby effecting treatment.

BRIEF DESCRIPTION OF THE FIGURES

FIGS. 6A-6B depict a schematic of tethers that contains two miRNA binding sites (FIG. 6A) and the nucleic acid sequences of miR-1 and mir-122 tethers (FIG. 6B).

FIGS. 14A-14D depict: (FIG. 14A) the structure of the miR-122 tethers T536 and T542; (FIG. 14B) the potency of silencing mRNA expression by the miR-122 T536 and T542 tethers in an rAAV luciferase assay in cultured human Huh7.5 hepatocarcinoma cells; (FIG. 14C) the structure of the miR-122 tethers T559 and T560; and (FIG. 14D) the potency of silencing mRNA expression by the miR-122 T559 and T560 tethers in an rAAV luciferase assay in cultured human Huh7.5 hepatocarcinoma cells.

(FIG. 16A) a schematic of a tether designed to target two different miRNAs to a target; (FIG. 16B) a recombinant adeno-associated virus (rAAV) vector designed to express two distinct, secreted luciferase proteins in mice; and (FIG. 16C) the in vivo efficacy of rAAV expression of dual secreted luciferases after infection at 3 different MOIs 10^10, 10^12 and 10^13.

FIGS. 18A-18C depict: (FIG. 18A) the nucleic acid sequences of tethers T567 and T568 that bind miR122 and APOC3 mRNA; and (FIG. 18B and FIG. 18C) the potency of miR-122 tethers T567 and T568 at silencing the APOC3 gene in human hepatocytes.

DETAILED DESCRIPTION

Figure 1:
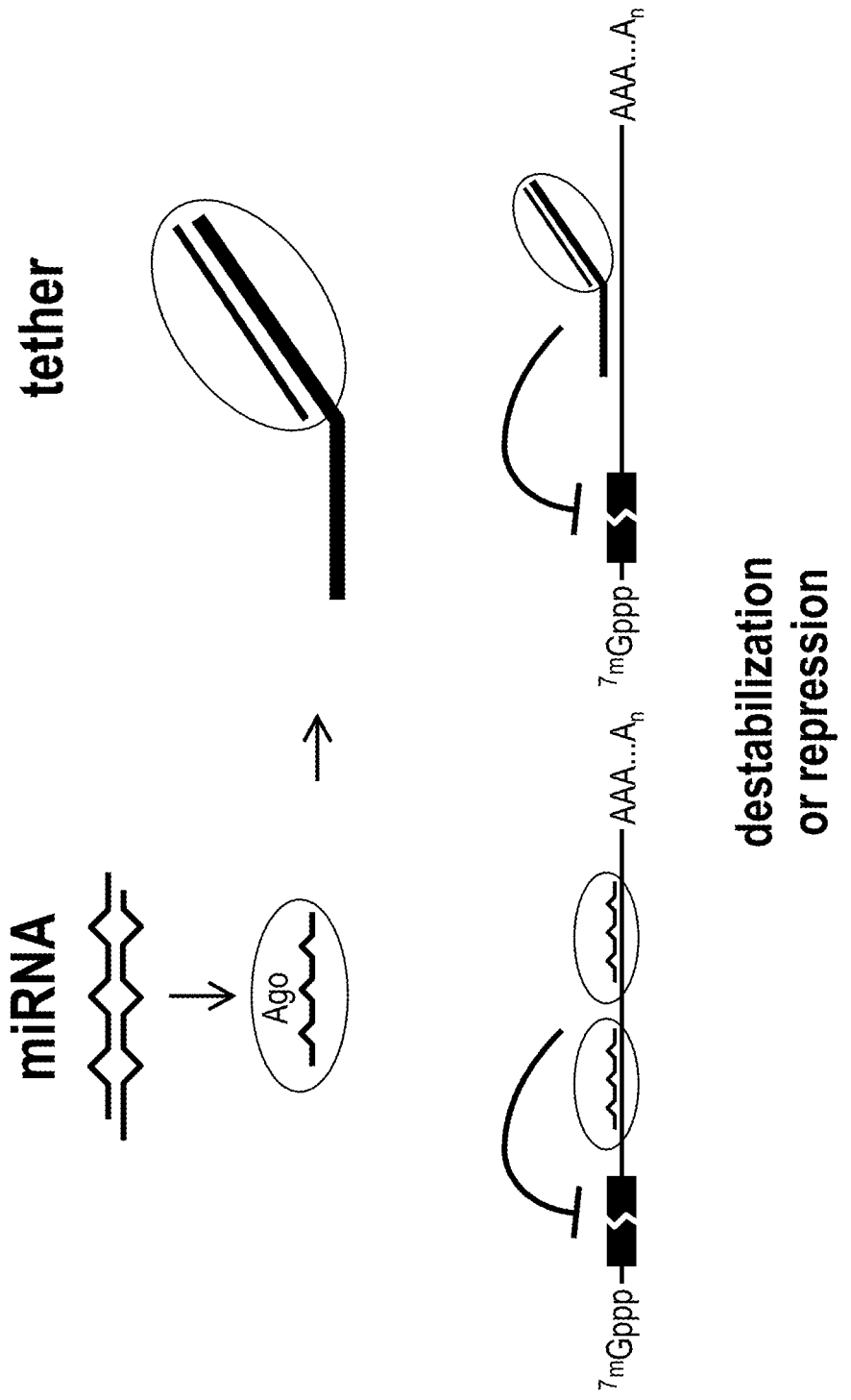
FIG. 1 depicts a schematic drawing of the oligonucleotide tether-mediated mRNA silencing technology.

The instant disclosure provides RNA-modulating agents that function to recruit one or more small regulatory RNA molecules (e.g., miRNA molecules, Y RNAs, and siRNAs) to a target mRNA thereby modulating (e.g., inhibiting) the translation of the target mRNA or destabilizing the mRNA. Also provided are miRNA inhibitors and diagnostic agents that have improved binding affinity for their target miRNAs. Methods for using the RNA-modulating agents, miRNA inhibitors and diagnostic agents are also provided.

The RNA-modulating agents disclosed herein have a number of advantageous features. For example, these RNA-modulating agents can modulate (e.g., silence) gene expression using a desired endogenous miRNAs, even though the target mRNA does not possess a binding site for that miRNA. Accordingly, the disclosed RNA-modulating agents can be used to target any gene in a cell or organism, including viral genes. The disclosed RNA-modulating agents also allow for cell type-specific or tissue-specific gene modulation (e.g., silencing) by recruitment of miRNA that are cell type-specific or tissue-specific (e.g., miR-122 which is liver-specific, and miR-1 which is muscle-specific).

I. DEFINITIONS

As used herein, the term "RNA-modulating agent" refers to a molecule comprising an mRNA binding sequence and a miRNA binding sequence. Non-limiting examples of RNA-modulating agents are set forth in US20050256072 and US20060293267, which are both incorporated herein by reference in their entirety.

As used herein, the term "mRNA binding sequence" refers to an oligonucleotide, or mimetic thereof, having a nucleotide sequence that is complementary to the nucleotide sequence of an mRNA.

As used herein, the term "miRNA binding sequence" refers to an oligoribonucleotide, or analogue thereof, having a nucleotide sequence that is complementary to the nucleotide sequence of an miRNA.

As used herein, the terms "microRNA" or "miRNA" refer to the class of naturally occurring, small, non-coding RNA molecules, about 21-25 nucleotides in length, that function to modulate gene expression in a variety of ways, including translational repression, mRNA cleavage, and deadenylation. The complete listing of published miRNA sequences as are set forth at mirbase.org.

As used herein, the term "complementary" refers to the ability of nucleotides, or analogues thereof, to form Watson-Crick base pairs. Complementary nucleotide sequences will form Watson-Crick base pairs and non-complementary nucleotide sequences will not.

As used herein, the term "position in the miRNA binding sequence corresponding to position 9 of the miRNA" refers to the nucleotide in an miRNA binding sequence that, in a perfect duplex of an miRNA binding sequence and its cognate miRNA, would form Watson-Crick base pairs with the 9th nucleotide of the miRNA (the miRNA being numbered from 5' to 3').

As used herein, the term "miRNA inhibitor" refers to a composition comprising an oligonucleotide sequence that is binds to a target miRNA and inhibits the function of the miRNA.

As used herein, the term "oligonucleotide" refers to a polymer of nucleotides comprising naturally occurring nucleotides, non-naturally occurring nucleotides, derivatized nucleotides, or a combination thereof. Non-limiting examples of nucleotides, and derivatives thereof, are set forth herein.

As used herein, the term "oligoribonucleotide" refers to a polymer of nucleotides comprising naturally occurring ribonucleotides, non-naturally occurring ribonucleotides, derivatized ribonucleotides, or a combination thereof. Non-limiting examples of ribonucleotides, and derivatives thereof, are set forth herein.

The term "RNA" or "RNA molecule" or "ribonucleic acid molecule" refers to a polymer of ribonucleotides. The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains.

II. RNA-MODULATING AGENTS, MIRNA INHIBITORS AND DIAGNOSTIC AGENTS

The instant disclosure provides RNA-modulating agents that function to recruit one or more small regulatory RNA molecules to a target mRNA thereby modulating the translation of the target mRNA. RNA-modulating agents can be designed to recruit any small regulatory RNA molecule to any target mRNA. Suitable small regulatory RNA molecules include, without limitation, miRNA, Y RNAs (e.g., hY4 RNA) and small interfering RNA (siRNA). Suitable target mRNA include, without limitation, nuclear mRNA, cytoplasmic mRNA, mitochondrial mRNA, chloroplast mRNA, and viral RNA.

In one aspect, the RNA-modulating agents comprise an mRNA binding sequence that is complementary to a portion of target mRNA, linked to one or more miRNA binding sequences that are complementary to one or more miRNA. An RNA-modulating agent can comprise any number of miRNA binding sequences (e.g., 1, 2, 3, 4, 5, 6, 7, 8, 9 or more). However, Applicants have demonstrated that RNA-modulating agents comprising 2 or more miRNA binding sequences are more potent at repressing gene expression than RNA-modulating agents comprising a single miRNA binding sequence. Limitations on the size of RNA-modulating agents make it practical for 2 or 3 miRNA binding sequences to be present. Where the RNA-modulating agent contains multiple miRNA binding sequences, each of the miRNA binding sequences can bind to the same or a different miRNA.

The miRNA binding sequence can be of any length sufficient to recruit the desired miRNA. In certain embodiments, the miRNA binding sequence is about 5 to about 25 nucleotides in length (e.g., about 5, 6, 7, 8, 9, 10, 11, 12, 13, 14, 15, 16, 17, 18, 19, 20, 21, 22, 23, 24, and 25).

The miRNA binding sequence can have any amount of complementarity with its cognate miRNA (e.g., 1, 2, 3 ,4, 5, 6, 7, 8, 9, 10, 11, 12, 13, 14, 15, 14, 15, 16, 17, 18, 19, 20, 21, 22, 23, 24, and 25 complementary nucleotides). The miRNA binding sequence can also be engineered to comprise specific combinations of Watson-Crick base pairs and mismatches with its cognate miRNA binding partner. In certain embodiments, the miRNA binding sequence is complementary to at least positions 2 to 8 of the miRNA. In certain embodiments, the miRNA binding sequence is complementary to only positions 2 to 8 of the miRNA. In certain embodiments, the miRNA binding sequence is not complementary to position 1 of the miRNA.

Applicants demonstrate herein that certain combinations of Watson-Crick base pairs and mismatches in the miRNA binding sequence can dramatically increase the potency (over 10-fold) of an RNA-modulating agent comprising two miRNA binding sequences. In certain embodiments, the miRNA binding sequences have a sequence complementary to at least positions 2 to 8 of a miRNA, but not complementary to positions 10 and 11 of the miRNA. In certain embodiments, the miRNA binding sequences have a sequence complementary to positions 2 to 8, and at least 12 to 25 of the miRNA (e.g., 12-15, 12-16, 12-17, 12-18, 12-19, 12-20, 12-21, 12-22, 12-23, 12-24, or 12-25), but not complementary to positions 1, 10 and 11 of the miRNA.

Applicants further demonstrate herein that the presence of adenosine at a position in the miRNA binding sequence corresponding to position 9 of the miRNA further increases the potency (over 2-fold) of an RNA-modulating agent comprising two seed-only miRNA binding sequences (FIGS. 12A and B). Accordingly, in certain embodiments, the miRNA binding sequences disclosed herein comprise an adenosine, or analogue thereof, at a position in the miRNA binding sequence corresponding to position 9 of the miRNA.

An RNA-modulating agent can comprise an mRNA binding sequence that is complementary to any portion of a target mRNA. In certain embodiments, the mRNA binding sequence is complementary to the 3'UTR of a target mRNA. The mRNA binding sequence should be of sufficient size to effectively bind the target mRNA. The length of the mRNA binding sequence will vary greatly depending, in part, on the length of the target mRNA and the degree of complementarity between the target mRNA and the mRNA binding sequence. In certain embodiments, the mRNA binding sequence is less than about 200, 100, 50, 30, 25, 20, 19, 18, 17, 16, 15, 14, 13, 12, 11, 10, 9, 8, 7, 6, or 5 nucleotides in length. In a particular embodiment, the targeting moiety is about 15 to about 25 nucleotides in length (e.g., 15, 16, 17, 18, 19, 20, 21, 22, 23, 24, or 25 nucleotides in length).

Any mRNA can be modulated using the RNA-modulating agents disclosed herein, including nuclear mRNA, cytoplasmic mRNA, mitochondrial mRNA, chloroplast mRNA, and viral RNA. When the target mRNA is a nuclear mRNA or cytoplasmic mRNA, the RNA-modulating agents generally cause gene silencing. However, when the target mRNA is a mitochondrial mRNA, the RNA-modulating agents can be used to increase expression of the encoded protein. In certain embodiments, the target mRNA encodes a protein that is overexpressed or overactive in a cell. In certain embodiments, the target mRNA encodes a protein that causes a disease or disorder in an organism (e.g., a human subject or plant), e.g., Huntington's disease (HD) or Amyotrophic lateral sclerosis (ALS). In certain embodiments, the target mRNA encodes a gain of function mutant protein (e.g., mutant huntingtin or SOD1 proteins). In certain embodiments, the target mRNA encodes a protein that is underexpressed or underactive (e.g., a mitochondrial encoded protein). In certain embodiments, the target mRNA encodes huntingtin, APOC3, or SOD1.

Any miRNA can be recruited using the RNA-modulating agents disclosed herein. Recruited miRNA can be naturally occurring, viral or synthetic. In certain embodiments, the miRNA is a tissue or cell type specific miRNA or viral miRNA. Recruitment of such miRNA allows for tissue specific or cell type specific gene modulation (e.g., gene silencing). Suitable miRNA include without limitation In certain embodiments, the miRNA is selected form the group consisting of miR122, miR-1, let-7, miR-103, miR-107 miR-216, miR-375, miR-124, miR-125, miR-128, miR-132, miR-134, miR-135, miR-138, miR-153, miR-143, miR-194, miR-133a, miR-206, miR-208, miR-142-3p, miR-143-5p, miR-181, miR-195, miR-221, miR-222, miR-192, miR-194, miR-204, miR-215, miR-30b, miR-30c, miR-122a, miR-152, miR-199, miR-215,miR-130, miR-24, miR-32, miR-189, miR-127, miR-150, miR-151, miR-212, miR-148, miR-204, miR-378, and a viral microRNA.

RNA-modulating agents can have a variety of architectures. The miRNA binding sequences can be linked together (i.e., in series or branching) on one end of the RNA-modulating agent (linked to either the 3' or 5' end of the mRNA binding sequence). Alternatively the miRNA binding sequences can be on either side of (i.e., flanking) the mRNA binding sequence in the RNA-modulating agent. In certain embodiments, the miRNA binding sequences are linked together in series in the RNA-modulating agent. In certain embodiments, the miRNA binding sequences are linked to the same end of the mRNA molecule in parallel branches in the RNA-modulating agent. In certain embodiments, the mRNA binding sequence is flanked by miRNA binding sequences in the RNA-modulating agent. In certain embodiments, the miRNA binding sequences are linked together in series, and linked to the 5' end of the mRNA binding sequence. In certain embodiments, the miRNA binding sequences are linked together in series, and linked to the 3' end of the mRNA binding sequence. In certain embodiments, the RNA-modulating agent is circular (e.g., a circular oligonucleotide).

In another aspect, the RNA-modulating agents comprise an mRNA binding sequence complementary to a portion of target mRNA linked to one or more Y RNA binding sequences complementary to one or more Y RNAs (e.g., hY1, hY3, hY4 and hY5, see Perreault *J, Mol. Biol. Evol.* 24 (8): 1678-89, which is incorporated herein by reference in its entirety). In certain embodiments, the Y RNA binding sequence binds to hY4.

RNA-modulating agents can be an oligonucleotide, or a mimetic thereof, or can comprise a mixture of nucleotides and other molecules. Where the RNA-modulating agents is an oligonucleotide, it generally has a length of about 20 to about 100 nucleotides (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100). In certain embodiments, the RNA-modulating agents are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target). Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5, 220,007; 5,256, 775; 5,366,878; 5,403,711; 5,491,133; 5,565,350; 5,623, 065; 5,652,355; 5,652,356; and 5,700,922, each of which is herein incorporated by reference in its entirety.

In certain embodiments, RNA-modulating agents comprise an mRNA binding sequence linked to two or more miRNA binding sequences. The mRNA binding sequence and miRNA binding sequences can be directly linked (e.g., via a phosphodiester or phosphothioate bond) to form a single continuous oligonucleotide, or they can be joined via a non-nucleotide linker (e.g. polyethylene glycol). The mRNA binding sequence and miRNA binding sequences can be joined in any orientation e.g., the 5'to 3' end linkage or additionally or alternatively the 5' to 5' end linkage).

RNA-modulating agents may comprise one more modified nucleotides. In certain embodiments, the RNA-modulating agents comprise at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2'O-methyl modifications on the ribose of pyrimidines, a basic residue or an inverted base at the 3' end of the RNA. In other preferred embodiments, one or more nucleotides are methylated (e.g., $N^6$-methyladenosine ($m^6A$) or 5-methylcytosine ($m^5C$)).

A number of nucleotide and nucleoside modifications have been shown to make an oligonucleotide more resistant to nuclease digestion, thereby prolonging in vivo half-life. Specific examples of modified oligonucleotides include those comprising backbones comprising, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, ~($CH_3$)~O~CH2 (known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—O—O—$CH_2$,); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497), each of which is herein incorporated by reference in its entirety. Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference in its entirety. Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol, 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991, each of which is herein incorporated by reference in its entirety. Cyclohexenyl nucleic acid oligonucleotide mimetics are described in Wang et al., J. Am. Chem. Soc., 2000, 122, 8595-8602, the contents of which is incorporated herein in its entirety.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference in its entirety.

In certain embodiments, RNA-modulating agents comprise one or more substituted sugar moieties, e.g., one of the following at the 2' position: OH, SH, $SCH_3$, F, OCN, $OCH_3OCH_3$, $OCH_3O(CH_2)nCH_3$, $O(CH_2)nNH_2$ or $O(CH_2)nCH_3$ where n is from 1 to about 10; Ci to CIO lower alkyl, alkoxyalkoxy, substituted lower alkyl, alkaryl or aralkyl; CI; Br; CN; CF3; OCF3; O-, S-, or N-alkyl; O-, S-, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacokinetic/pharmacodynamic properties of an oligonucleotide and other substituents having similar properties. A preferred modification includes 2'-methoxyethoxy [2'-O—$CH_2CH_2OCH_3$, also known as 2'-O-(2-methoxyethyl)] (Martin et al., Helv. Chim. Acta, 1995, 78, 486). Other preferred modifications include 2'-methoxy (2'-O—$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. "Locked" nucleic acids (LNA) may also be used in which the 2' hydroxyl of the ribose sugar is connected, e.g., by a methylene or ethylene bridge, to the 4' carbon of the same ribose sugar (e.g., a C2'-O,C4'-ethylene-bridged nucleotide). The sugar group can also contain one or more carbons that possess the opposite stereochemical configuration than that of the corresponding carbon in ribose. Thus, a modified RNA can include nucleotides containing e.g., arabinose, as the sugar. Oligonucleotides may also have sugar mimetics such as cyclobutyls in place of the pentofuranosyl group.

In certain embodiments, RNA-modulating agents comprise one or more base modifications and/or substitutions. As used herein, "unmodified" or "natural" bases include adenine (A), guanine (G), thymine (T), cytosine (C) and uracil (U). Modified bases include, without limitation, bases found only infrequently or transiently in natural nucleic acids, e.g., $N^6$-methyladenosine ($m^6A$), pseudouridine, hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic bases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions can also be included. These have been shown to increase nucleic acid duplex stability by 0.6-1.2 OC. (Sanghvi, Y. S., in Crooke, S. T. and Lebleu, B., eds., Antisense Research and Applications, CRC Press, Boca Raton, 1993, pp. 276-278). Further suitable modified bases are described in U.S. Pat Nos. 3,687,808, as well as 4,845, 205; 5,130,302; 5,134,066; 5,175, 273; 5,367,066; 5,432, 272; 5,457,187; 5,459,255; 5,484,908; 5,502,177; 5,525, 711; 5,552,540; 5,587,469; 5,596,091; 5,614,617; 5,750, 692, and 5,681,941, each of which is herein incorporated by reference.

It is not necessary for all positions in a given oligonucleotide to be uniformly modified, and in fact more than one of the aforementioned modifications may be incorporated in a single oligonucleotide or even at within a single nucleoside within an oligonucleotide.

In certain embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500. In certain embodiments, the RNA-modulating agent is linked (covalently or non-covalently) to one or more moieties or conjugates that enhance the activity, cellular distribution, or cellular uptake of the oligonucleotide. Such moieties include, without limitation, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937), each of which is herein incorporated by reference in its entirety. See also U.S. Pat. Nos. 4,828,979; 4,948,882; 5,218,105; 5,525, 465; 5,541,313; 5,545,730; 5,552, 538; 5,578,717, 5,580, 731; 5,580,731; 5,591,584; 5,109,124; 5,118,802; 5,138, 045; 5,414,077; 5,486,603; 5,512,439; 5,578,718; 5,608, 046; 4,587,044; 4,605,735; 4,667,025; 4,762,779; 4,789, 737; 4,824,941; 4,835,263; 4,876,335; 4,904,582; 4,958, 013; 5,082,830; 5,112,963; 5,214,136; 5,082,830; 5,112, 963; 5,214,136; 5,245,022; 5,254,469; 5,258,506; 5,262, 536; 5,272,250; 5,292,873; 5,317,098; 5,371,241, 5,391, 723; 5,416,203, 5,451,463; 5,510,475; 5,512,667; 5,514, 785; 5, 565,552; 5,567,810; 5,574,142; 5,585,481; 5,587, 371; 5,595,726; 5,597,696; 5,599,923; 5,599,928 and 5,688, 941, each of which is herein incorporated by reference in its entirety. In other exemplary embodiments, the moiety that enhances activity, cellular distribution, or cellular uptake is a glycan moiety, e.g., a multivalent GalNac moiety, e.g., trivalent or triantennary GalNac (see, e.g., Matsuda et. al., "siRNA conjugates carrying sequentially assembled trivalent N-Acetylgalactosamine linked through nucleosides elicit robust gene silencing in vivo in hepatocytes", ACS Chem. Biol., 2015, 10: 1181-187; Prakash et al., "Targeted Delivery of antisense oligonucleotides to hepatocytes using triantennary N-acetyl galactosamine improves potency 10-fold in mice", Nucleic Acids Research, 2014, which are incorporated by reference herein in their entireties).

In certain embodiments, RNA-modulating agents used to practice this invention are expressed from a recombinant vector. Suitable recombinant vectors include, without limitation, DNA plasmids, viral vectors or DNA minicircles. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989), Coffin et al. (Retroviruses. (1997) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors can be delivered as described herein, and persist in target cells (e.g., stable transformants).

In certain embodiments, RNA-modulating agents used to practice this invention are synthesized in vitro using chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68: 109; Beaucage (1981) Tetra. Lett. 22: 1859; U.S. Pat. No. 4,458,066, each of which is herein incorporated by reference in its entirety. In certain embodiments, RNA-modulating agents are synthesized in vitro using a variant T7 polymerase that permits enzymatic synthesis of fully 2'-O-methyl-modified nucleotides (e.g., 2'-O-methyl-ribonucleotides), for example, as set forth in Ibach et al., (2013) 168:287-295; Journal of Biotechnology, which is herein incorporated by reference in its entirety.

In another aspect, the instant disclosure provides an isolated miRNA binding sequence that is complementary to at least positions 2 to 8 of an miRNA, but not complementary to positions 10 and 11 of the miRNA. In certain embodiments, the miRNA binding sequence has one or more of the following properties: a) the miRNA binding sequence is complementary to positions 2 to 8, and 12 to 15, 12 to 16, or 12 to 17 of the miRNA, but not complementary to positions 10 and 11 of the miRNA; b) the miRNA binding sequence is not complementary to position 1 of the miRNA; c) the miRNA binding sequences is complementary to positions 2 to 8, and at least 12 to 25 of the miRNA (e.g., 12-15, 12-16, 12-17, 12-18, 12-19, 12-20, 12-21, 12-22, 12-23, 12-24, or 12-25), but not complementary to positions 1, 10 and 11 of the miRNA; d) the miRNA binding sequence is complementary to only positions 2 to 8 of the miRNA; e) the miRNA binding sequences has an adenosine, at a position in the miRNA binding sequence corresponding to position 9 of the miRNA; f) the miRNA binding sequences are about 8 to about 25 nucleotides in length.

The miRNA binding sequence can comprise any one or more of the altered nucleotides disclosed herein.

In another aspect, the instant disclosure provides a diagnostic agent comprising two or more miRNA binding sequence disclosed herein linked to a detectable label. In certain embodiments the detectable label is a fluorescent molecule.

In another aspect, the instant disclosure provides an oligonucleotide array comprising a plurality of the diagnostic agents disclosed herein.

In another aspect, the instant disclosure provides an miRNA inhibitor comprising two or more miRNA binding sequence disclosed herein.

III. METHODS OF USE

In one aspect the disclosure provides, a method of modulating expression of a target protein in a cell, the method comprising delivering into the cytoplasm of the cell an RNA-modulating agent, as disclosed herein, that binds to the mRNA encoding the target protein and modulates the translation of the target protein.

In general, the RNA-modulating agents disclosed herein result in gene silencing of the target mRNA. However, it has recently been demonstrated that miR-1 enhances expression of genes in muscle mitochondria. Accordingly, in certain embodiment, when a mitochondrial gene is targeted, the RNA-modulating agents disclosed herein result in enhanced expression of the protein encoded by the target mRNA. In certain embodiments, the cell is present in an organism (e.g., a mammal or a plant)

In another aspect the disclosure provides, a method of treating a subject having a disease or disorder characterized by or caused by: (a) the overexpression or overactivity of a normal cellular protein; (b) the underexpression or underactivity of a normal cellular protein; (c) the activity of a mutant protein; or (d) the activity of a viral RNA or protein, the method comprising administering to the subject an effective amount of an RNA-modulating agent, as disclosed herein, wherein the RNA-modulating agent binds to the mRNA encoding the protein and modulates expression of a protein.

In certain embodiments, the normal cellular protein is an apolipoprotein or a mutant apolipoprotein. In certain embodiments, the apolipoprotein or mutant apolipoprotein is selected from the group consisting of APOA-I, APOA-1 Milano, APOA-II, APOA-IV, APOA-V, APOB48, APOB100, APOC-I, APOC-II, APOC-III, APOC-IV, APOD, APOE, APOH, APOL1, APOL2, APOL3, APOL4, APOL5, APOL6 and APOLD1. In certain embodiments, the apolipoprotein is selected from the group consisting of APOA-I, APOA-1 Milano, APOA-II, APOA-IV, APOA-V, APOB48, APOB100, APOC-I, APOC-II, APOC-III and APOC-IV. In certain embodiments, the apolipoprotein is APOA-1 Milano or APOC-III. In certain embodiments, the apolipoprotein is APOA-1 Milano. In certain embodiments, the apolipoprotein is APOC-III.

In certain embodiments, the disease is a cardiovascular disease or metabolic disease. In certain embodiments, the cardiovascular disease is selected from the group consisting of coronary artery disease such as angina and myocardial infarction, stroke, hypertensive heart disease, rheumatic heart disease, cardiomyopathy, atrial fibrillation, congenital heart disease, endocarditis, aortic aneurysms, peripheral artery disease, venous thrombosis, dyslipidemia, atherosclerosis and hypertriglyceridemia, or a combination thereof. In certain embodiments, the metabolic disease is selected from the group consisting of obesity, diabetes, hyperglycemia, prediabetes, non-alcoholic fatty liver disease (NAFLD), metabolic syndrome, insulin resistance and diabetic dyslipidemia, or a combination thereof.

In another aspect, the instant disclosure provides a method of reducing the expression of APOC-III in a subject in need thereof, comprising administering to the subject an effective amount of an RNA-modulating agent, as disclosed herein. In certain embodiments the RNA-modulating agent binds to an mRNA encoding APOC-III and modulates expression of APOC-III.

In another aspect, the instant disclosure provides a method of detecting an miRNA is a sample, the method comprising contacting the sample with a diagnostic agent or an array, as disclosed herein, and detecting the formation of a complex between the diagnostic agent or array and the miRNA, wherein the presence of a complex between the diagnostic agent or array and the miRNA is indicative of the presence of the miRNA in the sample. In certain embodiments, the sample is a body fluid, tissue, or cell.

In another aspect, the instant disclosure provides a method of inhibiting the activity of an miRNA in a cell, the method comprising delivering into the cell an miRNA inhibitor, as disclosed herein, that binds to the miRNA and inhibits activity of the miRNA. In certain embodiments, the cell is present in an organism.

In another aspect, the instant disclosure provides a method of treating a subject having a disease or disorder characterized by or caused by the activity of an miRNA, the method comprising the method comprising administering to the subject an effective amount of an miRNA inhibitor, as disclosed herein, that binds to the miRNA inhibits activity of the miRNA, thereby effecting treatment.

Methods of treatment may be specifically tailored or modified, based on knowledge obtained from the field of pharmacogenomics. Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

RNA-modulating agents can be tested in an appropriate animal model. For example, a RNA-modulating agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, a RNA-modulating agent can be used in an animal model to determine the efficacy, toxicity, or side effects of treatment with such an agent. Alternatively, an agent can be used in an animal model to determine the mechanism of action of such an agent. An RNA-modulating agent modified for enhanced uptake into cells (e.g., liver cells) can be administered at a unit dose less than about 15 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA-modulating agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA silencing agent per kg of bodyweight. The unit dose, for example, can be administered by injection (e.g., intravenous or intramuscular), an inhaled dose, or a topical application. Particularly preferred dosages are less than 2, 1, or 0.1 mg/kg of body weight.

Delivery of a RNA-modulating agent directly to an organ or tissue can be at a dosage on the order of about 0.00001 mg to about 3 mg per organ/tissue, or preferably about 0.0001-0.001 mg per organ/tissue, about 0.03-3.0 mg per organ/tissue, about 0.1-3.0 mg per organ/tissue or about 0.3-3.0 mg per organ/tissue. In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In certain embodiments, a subject is administered an initial dose, and one or more maintenance doses of a RNA-modulating agent. The maintenance dose or doses are generally lower than the initial dose, e.g., one-half less of the initial dose. A maintenance regimen can include treating the subject with a dose or doses ranging from 0.01 mg/kg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in condition, e.g., changes in percentage body fat. The dosage of the compound may either be increased in the event the patient does not respond significantly to current dosage levels, or the dose may be decreased if a decrease in body fat is observed, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., sub-cutaneous, intravenous, intraperitoneal, intracisternal or intracapsular), or reservoir may be advisable. In one embodiment, a pharmaceutical composition includes a plurality of RNA-modulating agent species. In another embodiment, the RNA-modulating agent species has sequences that are non-overlapping and non-adjacent to another species with respect to a naturally occurring target sequence. In another embodiment, the plurality of RNA-modulating agent species is specific for different naturally occurring target genes. In another embodiment, the RNA-modulating agent is allele specific. In another embodiment, the plurality of RNA-modulating agent species target two or more SNP alleles (e.g., two, three, four, five, six, or more SNP alleles).

Following successful treatment, it may be desirable to have the patient undergo maintenance therapy to prevent the recurrence of the disease state, wherein the compound of the invention is administered in maintenance doses, ranging from 0.01 mg per kg to 100 mg per kg of body weight (see U.S. Pat. No. 6,107,094).

The concentration or amount of RNA-modulating agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a RNA-modulating agent can include a single treatment or, preferably, can include a series of treatments. It will also be appreciated that the effective dosage of a RNA-modulating agent for treatment may increase or decrease over the course of a particular treatment. Changes in dosage may result and become apparent from the results of diagnostic assays as described herein. For example, the subject can be monitored after administering a RNA-modulating agent composition. Based on information from the monitoring, an additional amount of the RNA-modulating agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g., a gene that produces a target mRNA. The transgenic animal can be deficient for the corresponding endogenous mRNA. In another embodiment, the composition for testing includes a RNA-modulating agent that is complementary, at least in an internal region, to a sequence that is conserved between a nucleic acid sequence in the animal model and the target nucleic acid sequence in a human.

RNA-modulating agents may be directly introduced into a cell; or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The RNA-modulating agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The RNA-modulating agents may be introduced along with other components e.g., compounds that enhance RNA-modulating agent uptake by a cell.

IV. PHARMACEUTICAL COMPOSITIONS

In one aspect, the methods disclosed herein can include the administration of pharmaceutical compositions and formulations comprising RNA-modulating agents capable of modulating the expression of at least one target mRNA.

In certain embodiments, the compositions are formulated with a pharmaceutically acceptable carrier. The pharmaceutical compositions and formulations can be administered parenterally, topically, by direct administration into the gastrointestinal tract (e.g., orally or rectally), or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., Remington: The Science and Practice of Pharmacy, 21st ed., 2005.

The RNA-modulating agents can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations of the invention can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragées, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragée cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In certain embodiments, oil-based pharmaceuticals are used for administration of the RNA-modulating agents. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

In certain embodiments, the pharmaceutical compositions and formulations are in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

In certain embodiments, the pharmaceutical compositions and formulations are administered by in intranasal, intraocular and intravaginal routes including suppositories, insufflation, powders and aerosol formulations (for examples of steroid inhalants, see e.g., Rohatagi (1995) J. Clin. Pharmacol. 35: 1 187-1193; Tjwa (1995) Ann. Allergy Asthma Immunol. 75: 107-1 11). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In certain embodiments, the pharmaceutical compositions and formulations are delivered transdermally, by a topical route, formulated as applicator sticks, solutions, suspensions, emulsions, gels, creams, ointments, pastes, jellies, paints, powders, and aerosols.

In certain embodiments, the pharmaceutical compositions and formulations are delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In certain embodiments, the pharmaceutical compositions and formulations are parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In certain embodiments, the pharmaceutical compounds and formulations are lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL nucleic acid, about 15 mg/mL sucrose, about 19 mg/mL NaCl, and a sodium citrate buffer having a pH greater than 5.5 but less than 6.5. See, e.g., US20040028670.

In certain embodiments, the pharmaceutical compositions and formulations are delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46: 1576-1587.

The formulations of the invention can be administered for prophylactic and/or therapeutic treatments. In certain embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84: 1144-1146; Rohatagi (1995) Pharmazie 50:610-613; Brophy (1983) Eur. J. Clin. Pharmacol. 24: 103-108; Remington: The Science and Practice of Pharmacy, 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate. Single or multiple administrations of formulations can be given depending on for example: the dosage and frequency as required and tolerated by the patient, the degree and amount of cholesterol homeostasis generated after each administration, and the like. The formulations should provide a sufficient quantity of active agent to effectively treat, prevent or ameliorate conditions, diseases or symptoms.

In certain embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington: The Science and Practice of Pharmacy, 21st ed., 2005.

Several studies have reported successful mammalian dosing using RNA agents. For example, Esau C, et al., (2006) Cell Metabolism, 3(2): 87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, nontoxic dose. Another study by Krutzfeldt J., et al., (2005) Nature 438, 685-689, injected antagomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg per kg LNA-antimiR, leading to a long-lasting and reversible decrease in total plasma cholesterol without any evidence for LNA-associated toxicities or histopathological changes in the study animals.

In certain embodiments, RNA-modulating agents used to practice this invention are administered through expression from a recombinant vector. Suitable recombinant vectors include, without limitation, DNA plasmids, viral vectors or DNA minicircles. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors can be delivered as described herein, and persist in target cells (e.g., stable transformants).

The RNA-modulating agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The RNA-modulating agents may be introduced along with other components e.g., compounds that enhance RNA-modulating agent uptake by a cell.

In certain embodiments, the methods described herein include co-administration of RNA-modulating agents with other drugs or pharmaceuticals.

V. EXEMPLIFICATION

The present invention is further illustrated by the following examples which should not be construed as further limiting. The contents of Sequence Listing, figures and all references, patents and published patent applications cited throughout this application are expressly incorporated herein by reference.

Furthermore, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition (1989)

Cold Spring Harbor Laboratory Press, Cold Spring Harbor, N.Y. (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology,* John Wiley & Sons, Inc. (1994).

Figure 22:
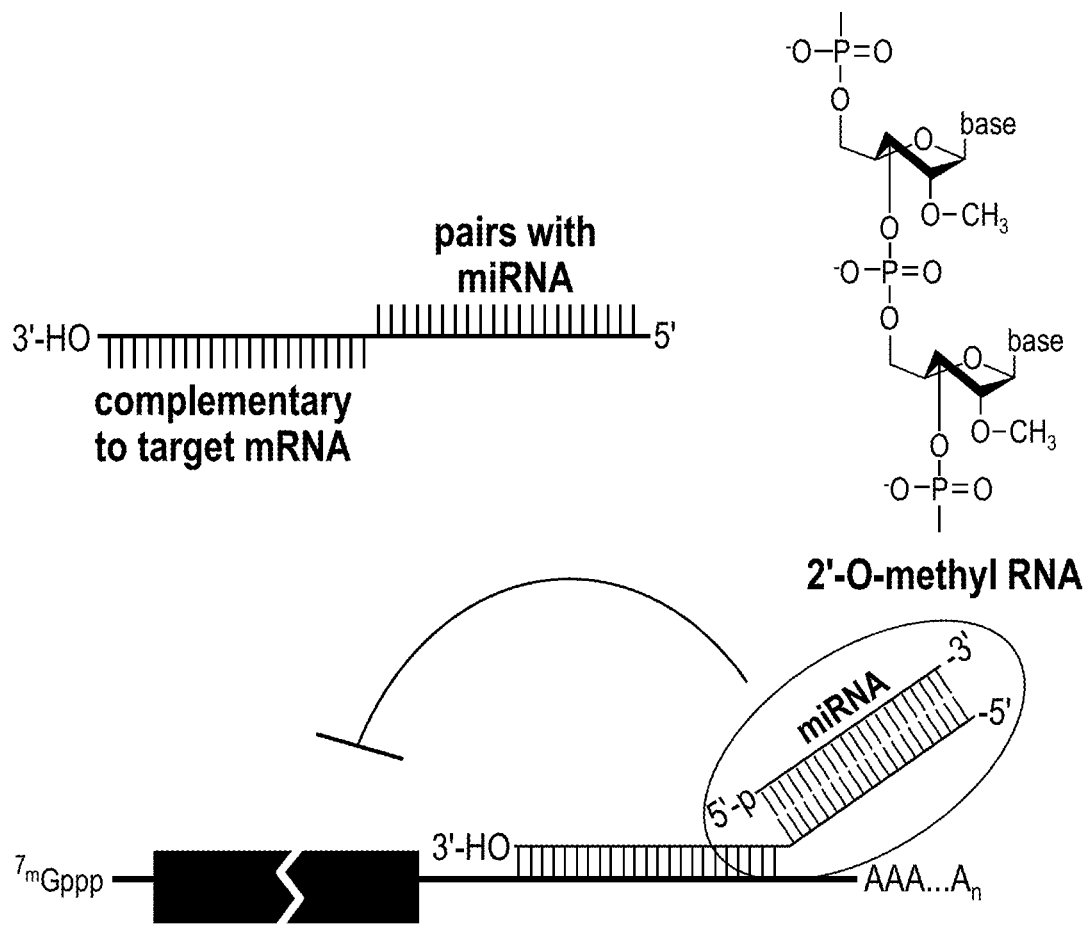
FIG. 22 depicts a schematic of engineered dual function 2'-O-methyl-modified RNA tethers.

To trigger effective RNAi in vivo, a double-stranded siRNA must (1) retain function but resist nucleolytic degradation; (2) load its antisense strand into Argonaute2 protein, the only one of the four mammalian Argonautes that can mediate RNAi; and (3) silence the target gene only in the intended cell type or target tissue. Redirecting endogenous microRNAs (miRNA) to silence genes that they do not normally target solves these challenges that limit the successful use of siRNAs in vivo. Certain embodiments presented herein describe a stabilized, synthetic oligonucleotide tether that recruits an endogenous miRNA to a specific target mRNA. The oligonucleotide tether contains one region complementary to the target mRNA and another to an abundant endogenous miRNA (FIG. 22). The tether binds endogenous miRNA-loaded Argonaute complexes and links them to the mRNA. In vivo in mouse liver and in cultured human hepatocyte cell lines, a tether can readily silence the target luciferase reporter expressed from rAAV without altering expression of the control luciferase. Tethers designed to recruit miR-122 to the 3' UTR of an endogenous mRNA reduced mRNA abundance in cultured human hepatocytes by ~50%. The results described herein suggest that it is possible to (1) redirect an endogenous miRNA to silence an mRNA with no binding sites for that miRNA and (2) design the tether to silence only in specific tissues by choosing a miRNA with an appropriate expression pattern.

EXAMPLE 1

Cell Type-Specificity of Tether-Mediated Gene Silencing

EXAMPLE 1.1

Tether-Mediated Silencing of Luciferase with miR-122

Currently, siRNA-directed silencing of an mRNA in a specific cell type relies on targeted delivery of the siRNA to those cells by tissue-specific nanoparticle formulations or attachment of specific ligands to the siRNA. In contrast, tether-mediated gene silencing occurs only in one or a small number of tissues, irrespective of the specificity of tether delivery, because silencing occurs only in those cells that produce the miRNA.

An oligonucleotide tether redirects endogenous microRNAs to silence genes that they do not normally target. The tether is an endonuclease-resistant, modified RNA that combines a sequence complementary to the target mRNA with a second sequence complementary to an abundant endogenous miRNA found in the tissue of interest. The tether binds endogenous miRNA-loaded Argonaute complexes and recruits them to the mRNA (FIG. 1).

Figure 2:
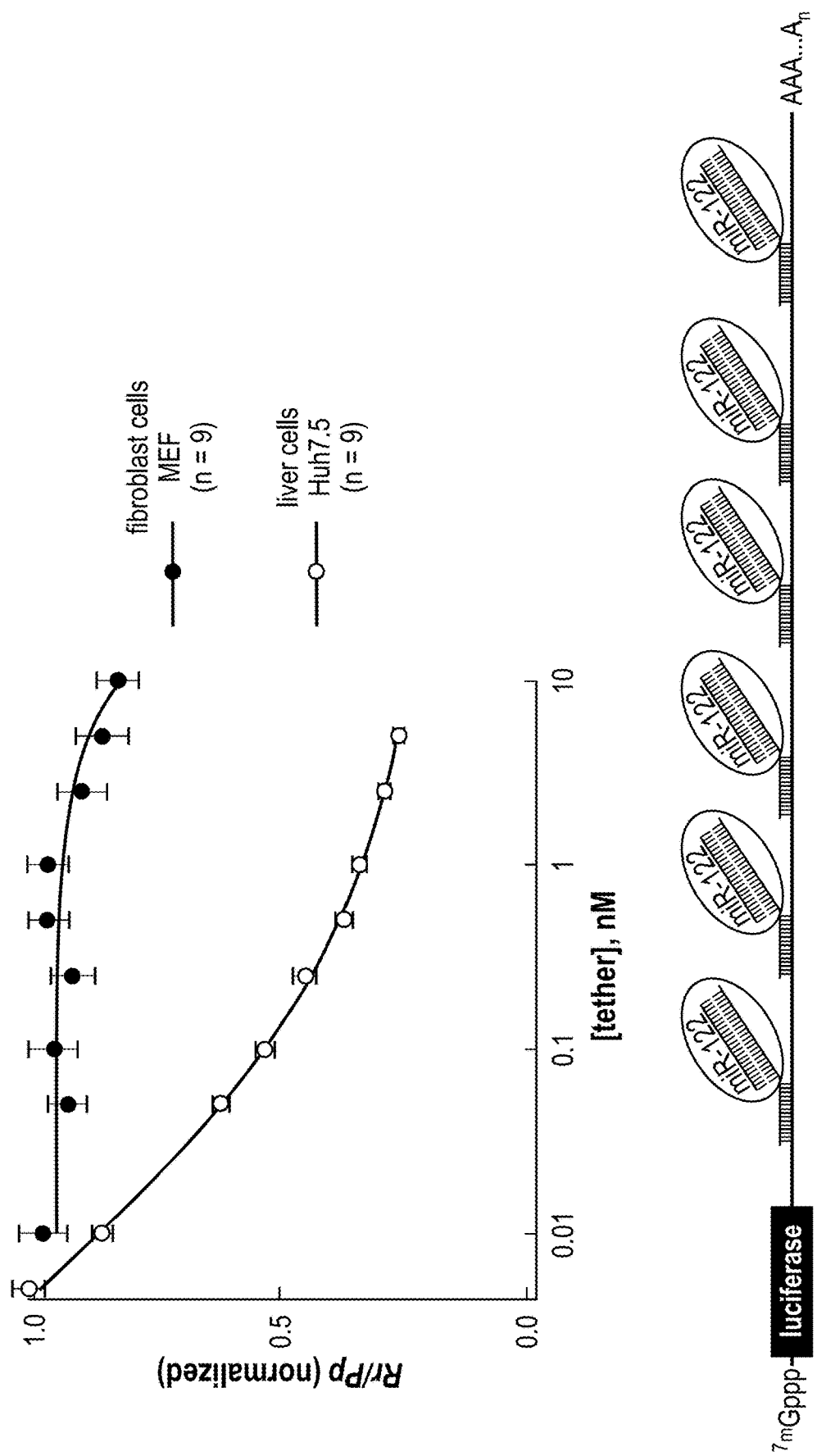
FIG. 2 depicts a luciferase reporter assay that demonstrates the cell-type specificity the oligonucleotide tether-mediated mRNA silencing technology.

Oligonucleotide tether-mediated gene silencing was assessed in a cell expressing the miRNA to which the tether was designed to recruit against gene silencing in a cell type lacking the miRNA. miR-122 was selected as a model because it is uniquely expressed in hepatocytes, where it is present at 50,000 molecules per cell and accounts for more than 70% of all miRNAs in liver (Chang et al., 2004). A tether was designed that pairs to miR-122 and was evaluated for luciferase reporter silencing at 10 tether concentrations in human Huh7.5 hepatocyte cells, which expresses high levels of miR-122, and in murine embryonic fibroblasts (MEF) cells, which lack miR-122. 80% silencing of the reporter was observed in Huh7.5 cells but no silencing was seen in MEF cells, even at 20 nM, the highest tether concentration transfected (FIG. 2). Tether-mediated gene silencing is thus the only therapeutic RNAi strategy that limits gene silencing to the targeted cell type even when the therapeutic agent is delivered systemically to many tissues.

EXAMPLE 1.2

Tether-Mediated Gene Silencing of Luciferase with miR-A or let-7

Figure 20A:
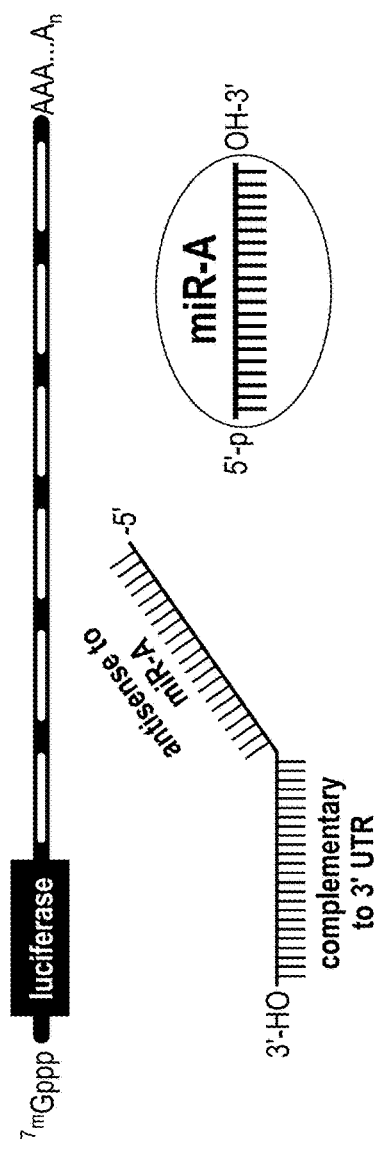
FIG. 20A shows a diagram of experimental design components used in the first proof-of-concept experiments to tether RISC to a luciferase reporter gene containing 6 sites for the tether to bind in the 3'UTR, a cartoon of the tether shows a region complementary to the target 3' UTR and a region that is antisense to a microRNA, also a cartoon of RISC containing an artificial exogenous miRNA, miR-A.
Figure 20B:
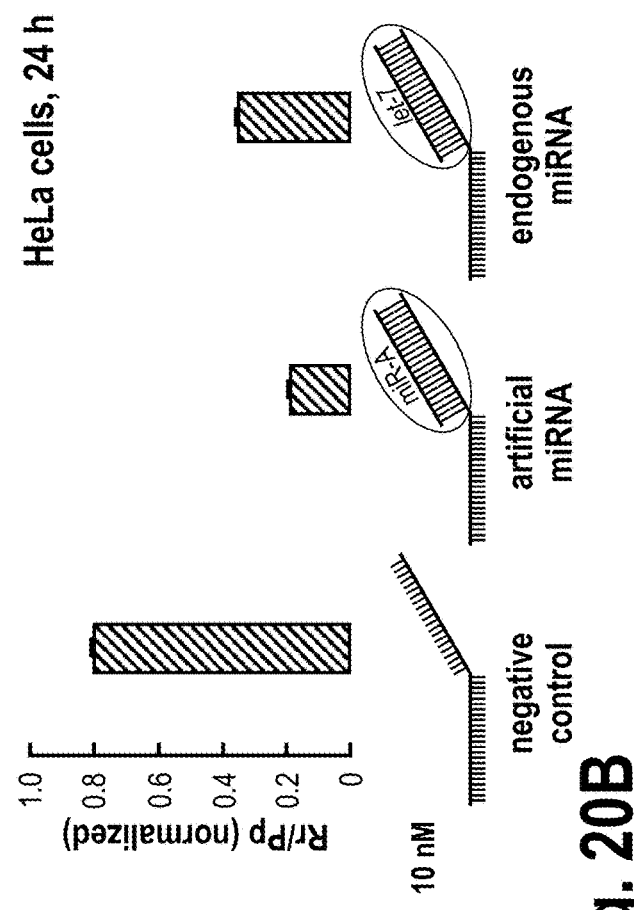
FIG. 20B shows normalized luciferase reporter activity in HeLa cells treated with 10 nanomolar control tether, or tether that can recruit the exogenous artificial miR-A, or a tether that recruits endogenous let-7 microRNA to the 3' UTR of the Renilla luciferase reporter gene, compared to an artificial microRNA or siRNA that can bind directly to the target mRNA.
Figure 20C:
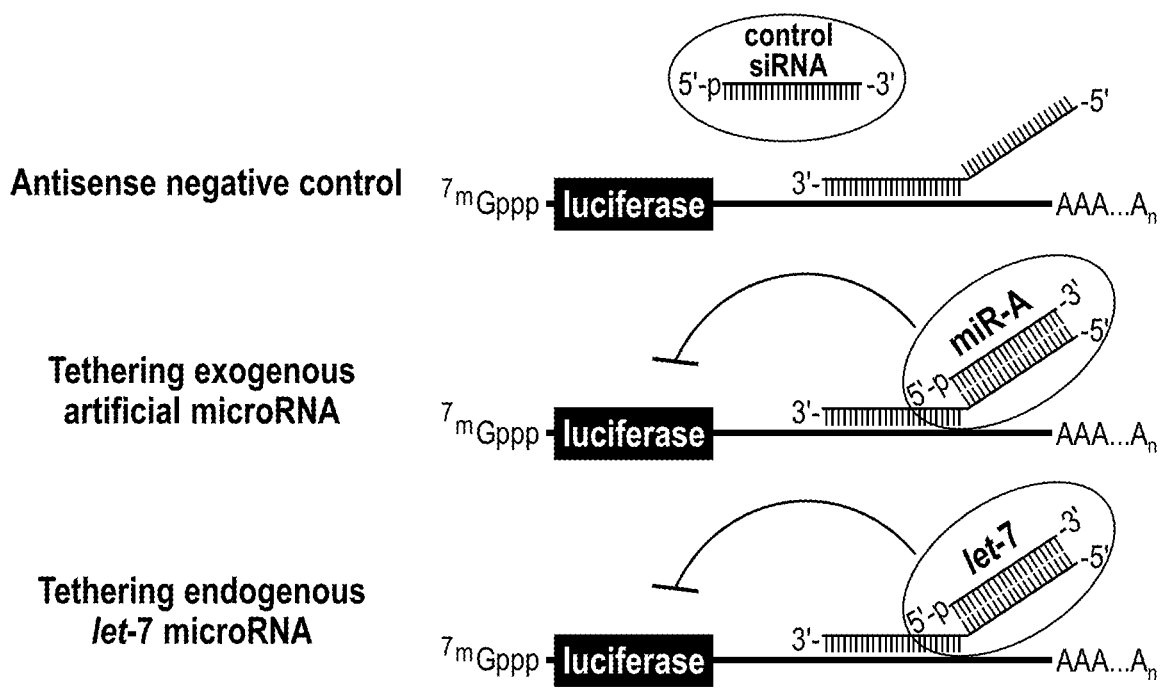
FIG. 20C shows a diagram of the experimental and control tethers used in the experimental system used in FIG. 20A and B.

We evaluated, in cultured human cells, the ability of an exogenous siRNA to pair with a tether and recruit an Argonaute complex to the 3' untranslated region (3' UTR) of a luciferase reporter containing six binding sites for the tether (FIGS. 20A and C). In these experiments, we used an artificial siRNA that was the same sequence as a plant microRNA, miR166 that does not exist in human cells. This allowed us to evaluate the effect of the tether, in the absence of the miRNA, when it is unable to recruit Argonaute to the 3' UTR of the luciferase reporter. When we transfected the artificial miRNA, miR-A, with the tether and reporter, expression of the reporter was silenced by 80% (FIG. 20B). When the tether and reporter genes were transfected with a control siRNA, that cannot pair to the tether, the reporter was not silenced indicating that the robust silencing we observed was due specifically to the presence of an Argonaute silencing complex being recruited, by the tether, to the 3' UTR of the reporter mRNA. To test whether a tether could recruit an endogenous miRNA to silence the reporter, we created a tether that pairs to an endogenous miRNA, let-7, that is expressed in HeLa cells. When 10 nM of this tether was co-transfected with the reporter, we observed ~60% silencing that was equal to the silencing caused by a miRNA that paired directly to the mRNA (FIG. 20B).

EXAMPLE 1.3

Tether-Mediated Gene Silencing of SOD1 with miR-122

Preliminary experiments generally have employed a luciferase reporter gene containing six tether binding sites. However, a therapeutic target mRNA is unlikely to contain six identical tether binding sites. Furthermore, clinical trials using a cocktail of six different tethers targeting a single mRNA are undesirable. To determine whether efficient silencing could be mediated by a tether that recruits miR-122 to a single site in the 3' UTR of an endogenous mRNA, a tether was designed that recruits miR-122 to a single, 15-nucleotide long site in the 3' UTR of human SOD1 (hsSOD1) mRNA. SOD1 has been implicated in the pathogenesis of ALS and is therefore a target of particular interest.

Figure 3:
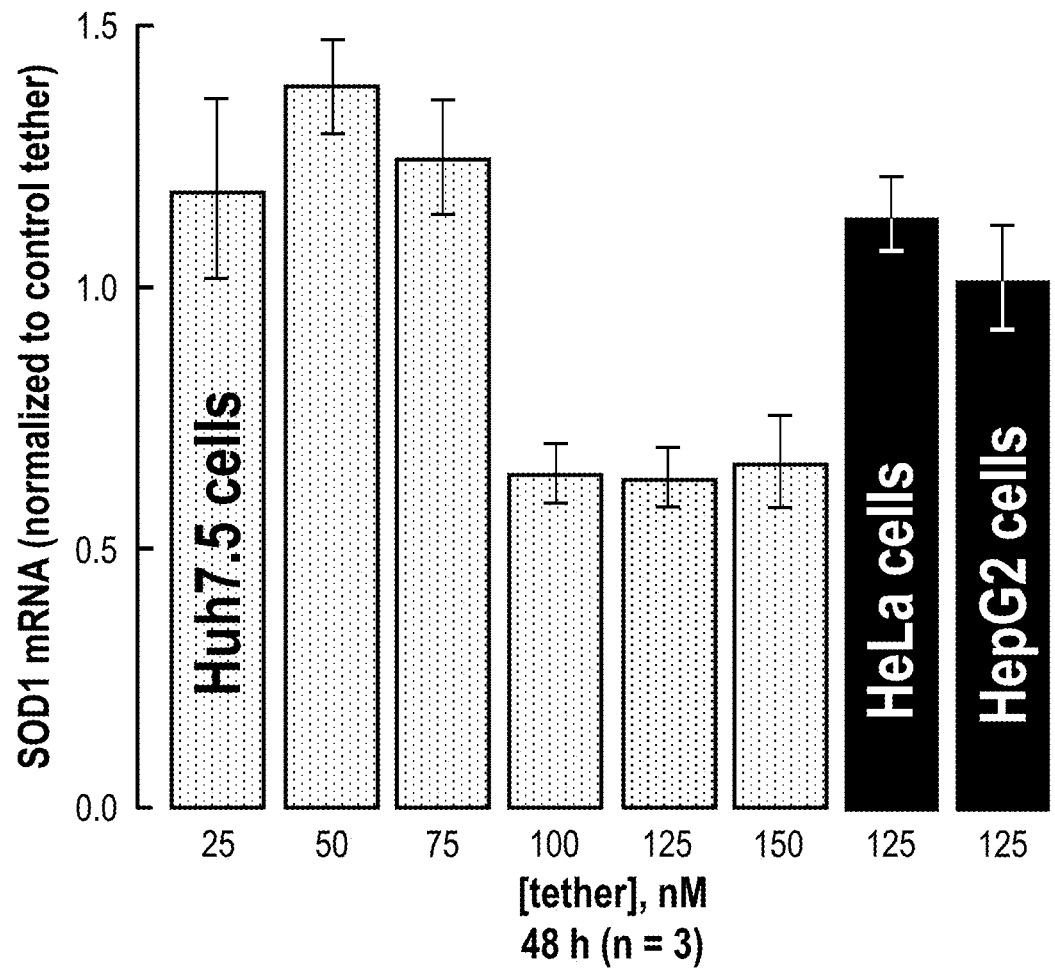
FIG. 3 depicts quantitative reverse transcriptase polymerase chain reaction (qRT-PCR) assay that demonstrates the cell-type specificity the oligonucleotide tether-mediated mRNA silencing technology for silencing an endogenous mRNA, SOD1.
Figure 3:
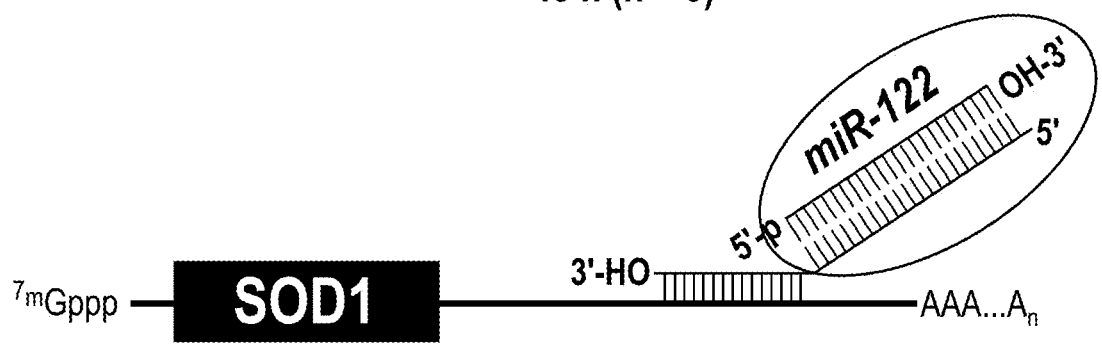

The human hepatocyte cell line Huh7.5 abundantly expresses miR-122, whereas HepG2 cells, which derive from a well-differentiated hepatocellular carcinoma, do not (Jopling et al., 2005). Huh7.5 cells were transfected with a miR-122/hsSOD1 tether at concentrations from 25-150 nM. In parallel, HepG2 and HeLa cells were transfected with the highest concentration of tether, 150 nM. After 48 h, total RNA was isolated from the cells and reverse transcribed. The level of hsSOD1 mRNA was determined by quantitative real-time RT-PCR using GAPDH mRNA as an internal control. The data show that >100 nM tether caused a 50% decrease in the level of SOD1 mRNA in the Huh7.5 cells (FIG. 3). In contrast, in the cells that do not express miR-122, 150 nM tether did not alter the abundance of SOD1 mRNA, compared to a control tether that binds neither hsSOD1 mRNA nor miR-122. These data establish the cell type-specificity of tether-mediated gene silencing for an endogenous and clinically relevant gene bearing just a single tether-binding site.

EXAMPLE 2

Figure 4:
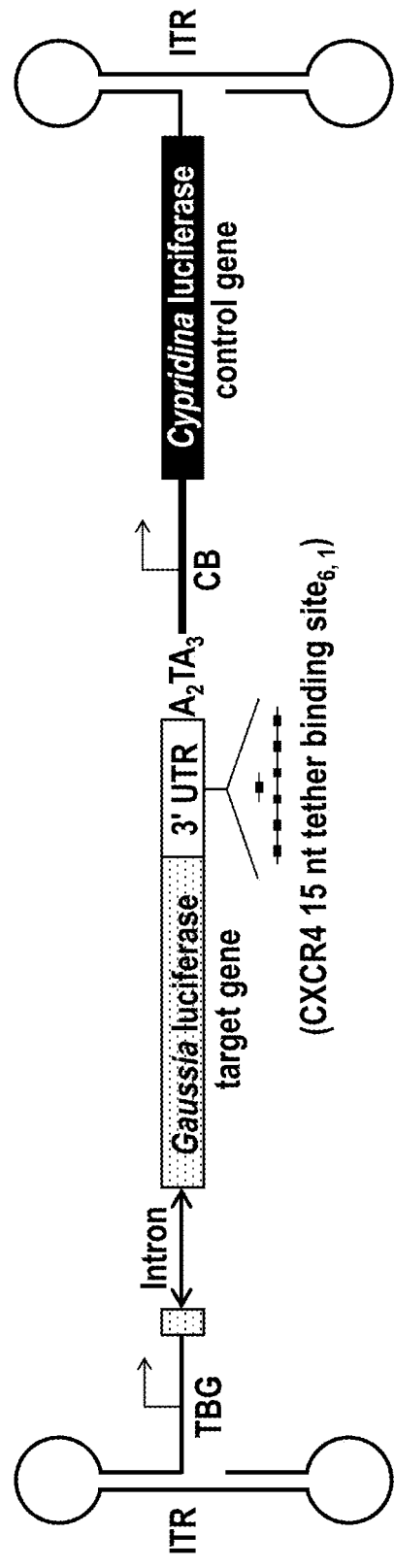
FIG. 4 depicts a recombinant adeno-associated virus (rAAV) vector designed to express two distinct, secreted luciferase proteins in mice.

Efficacy, Durability and Safety of Tether Oligonucleotides that Redirect an Endogenous microRNA to a Reporter Gene In Vivo To test whether oligonucleotide tethers may provide a more specific alternative to siRNA and antisense technology for silencing genes in vivo, a secreted dual luciferase reporter was created to monitor gene silencing over time in living mice. A recombinant adeno-associated virus (rAAV) was engineered to express two distinct, secreted luciferase proteins in mice (FIG. 4). One luciferase serves as a silencing target while the other provides an internal control. In cultured human hepatocyte cell lines, a tether can readily silence the target luciferase reporter without altering expression of the control luciferase. Because both luciferases are secreted, silencing can be measured in the culture supernatant. In adult mice, gene silencing can be assayed by monitoring the rAAV-expressed, secreted luciferases from blood samples. A proof-of concept in vivo experiment was designed to test whether a tether can silence the Gaussia luciferase reporter target gene expressed in mouse liver via the thyroxine-binding globulin (TBG) promoter. The control gene, Cypridina luciferase, is expressed in all cells from the chicken β-actin promoter. Secreted luciferases are measured from blood samples collected by either lateral tail vein puncture or retro-orbital bleeding, over multiple time points without having to sacrifice the animals. Such a strategy both minimizes inter-animal variability (i.e., each animal is only compared to itself over time) and reduces the number of mice required to obtain statistically meaningful data.

EXAMPLE 2.1

Figure 14A:
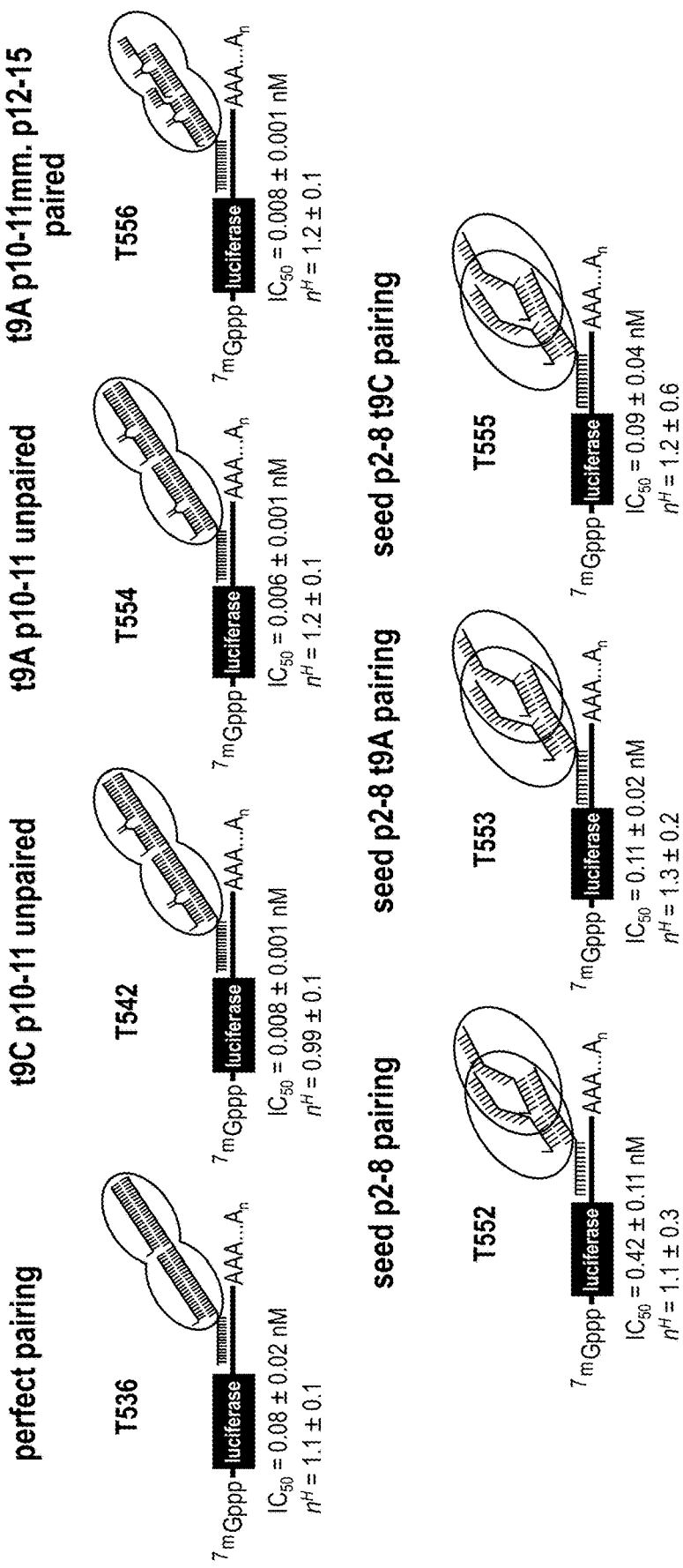
Figure 18C:
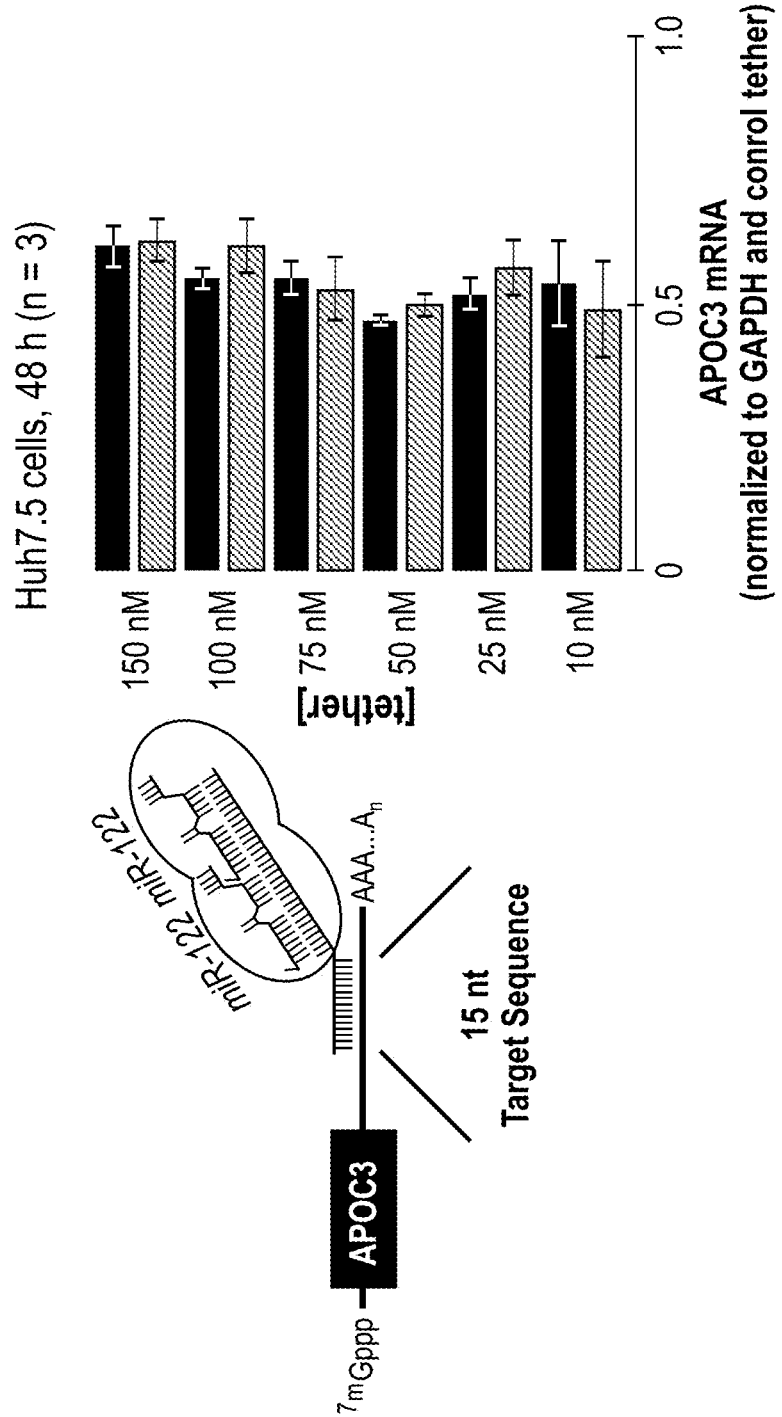
Figure 19A:
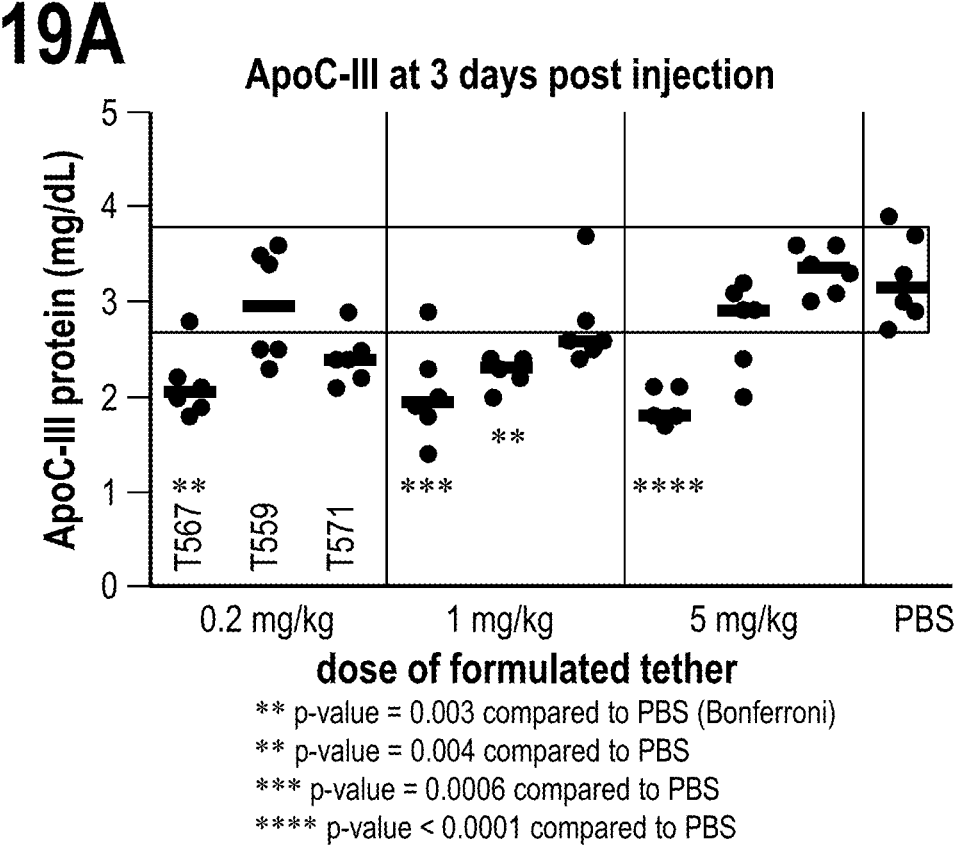
FIG. 19A shows serum ApoC3 levels (mg/dL) in mice 3 days after they were treated with 3 different doses (0.2 mg/kg, 1 mg/kg, or 5 mg/kg) of a tether (T567: experimental APOC3/miR-122 tether, T559: miR-122 inhibition control tether, T571: APOC3 antisense silencing control tether).

Silencing Expression of Gaussia Luciferase Target mRNA by Tethering miR-122 Argonaute Complex to the 3' UTR of the Target mRNA For the in vivo tether-mediate gene silencing experiments, a recombinant adeno-associated virus (rAAV) was engineered to express two distinct, secreted luciferase proteins in mice. One luciferase served as a silencing target while the other provided an internal control. The miR-122 tethers T536 and T542, that were subsequently tested in vivo (FIG. 17), readily suppressed expression of the luciferase target when the reporter gene was expressed from the rAAV plasmid in cultured human Huh7.5 hepatocarcinoma cells (IC50=0.08±0.02 nM and 0.008±0.001 nM, respectively) (FIGS. 14A and B). The latest design of tether pairings, T559 and T560, had even greater potency and readily suppressed expression of the luciferase target when the reporter gene was expressed from the rAAV plasmid in cultured human Huh7.5 hepatocarcinoma cells (IC50=0.003±0.001 nM and 0.002±0.001 nM, respectively) (FIGS. 14C and D). Tethers T567 and T568, based on the type of pairing in T559 and T560, were effective in vitro for silencing APOC3 (FIG. 18) and were tested in vivo for silencing APOC3 (FIGS. 19A, B and C).

EXAMPLE 2.2

Delivery of Tethers to the Mouse Liver

To be effective, therapeutic oligonucleotides must exit the circulatory system and enter the target tissue, transit the cell membrane, and, finally, escape from endosomal vesicles into the cytoplasm. The size of a non-conjugated therapeutic RNA is 7-20 kDa; molecules smaller than 50 kDa are filtered by the kidneys and excreted. Transfer of therapeutic RNA from the blood to the target tissue is a challenge because anything larger than 5 nm diameter, including therapeutically complexed RNA, cannot cross the capillary endothelium and will remain in circulation until filtered by the kidneys. Local delivery of therapeutic RNA by injection increases its bioavailability in the target tissue and minimizes uptake in non-target tissues, but is limited to eye, skin, mucous membranes and tumors. Systemic delivery into the bloodstream is challenged by phagocytic immune cells, such as macrophages and monocytes, which remove complexed RNAs from the body. Typically, antisense oligonucleotides delivered to muscle, heart and bone end up not in the cytoplasm, where they can find their target mRNAs, but in phagolysosomes. Cells of the liver, spleen and some tumors allow molecules up to 200 nm in diameter to enter and so the liver is among the most successful organs for delivering therapeutic RNAs. To target tether molecules to the liver, tethers were formulated in novel lipidoids called C12-200. The lipidoid can deliver microgram per kilogram amounts of siRNA to liver in mouse and cynomolgus monkeys without toxicity (Love et al., 2010). Other lipid-based delivery carriers require an siRNA dose of at least 1 milligram per kilogram to achieve 50% silencing of a target gene. In contrast, when the C12-200 lipidoid was used to deliver siRNA at a dose of 10 microgram per kilogram, 50% silencing of Factor VII mRNA was achieved in mice. A dose of 1 milligram per kilogram of C12-200 formulated tether in a 150 microliter volume can be delivered in to the mouse liver via a single tail vein injection. Gaussia luciferase gene expression will be monitored by assaying luciferase activity in blood samples from mice that received the experimental tethers and compared to luciferase activity in blood from mice that received a control tether that does not target the reporter or bind miR-122. The primary goal for this experiment is to establish proof of concept in vivo tether-mediated gene silencing. If the tethers are able to silence the reporter gene, the target gene expression level will be allowed to recover to the pre-dosing level and the same dose of tether will be repeated. The secondary goal is to evaluate the degree and duration of tether gene silencing.

EXAMPLE 2.3

Safety

A single-stranded tether molecule could signal host pattern recognition receptors such as Toll-like receptors, particularly, TLR7/8. Blood will be collected from the mice 1, 2, 4, 6 and 8 weeks after injection to measure innate immune activation in response to the tether by monitoring serum inflammatory cytokine levels (e.g., TNFa, IL-6, IL-1β, MCP-1), liver function (serum transaminases ALT and AST), and tumor biomarker profile (serum α-fetoprotein). A portion of each blood sample will be used to measure Gaussia and Cypridina luciferase activity, so as to determine the amount of gene silencing. The mice will be monitored for body weight, temperature and activity biweekly.

Low miR-122 levels have been associated with hepatocellular carcinoma (HCC) in rodents and humans, although no direct causal link has been established (Kutay et al., 2006; Bai et al., 2009; Coulouarn et al., 2009; Tsai et al., 2009). It is possible that tethers may reduce the cellular concentration of miR-122 such that tether treated mice could have an increased risk of developing HCC. Human Hepatitis C virus (HCV), a single-stranded, positive sense RNA virus, genotypes 1a,b and 2a require miR-122 to bind to two adjacent sites in the 5' UTR in order to replicate. HCV can persist in the host for decades without causing HCC and worldwide HCV is the cause of only 25% of HCC cases. Thus, due to the extremely high abundance of miR-122, it is possible that there is a therapeutic window in which a redirection of miR-122 for tether gene silencing will be efficacious for silencing host mRNA targets or viral target RNAs without increased risk of HCC.

EXAMPLE 3

Tether with Improved Gene Silencing Potency

EXAMPLE 3.1

Tethers Containing Multiple miRNA Binding Sites

Figure 5:
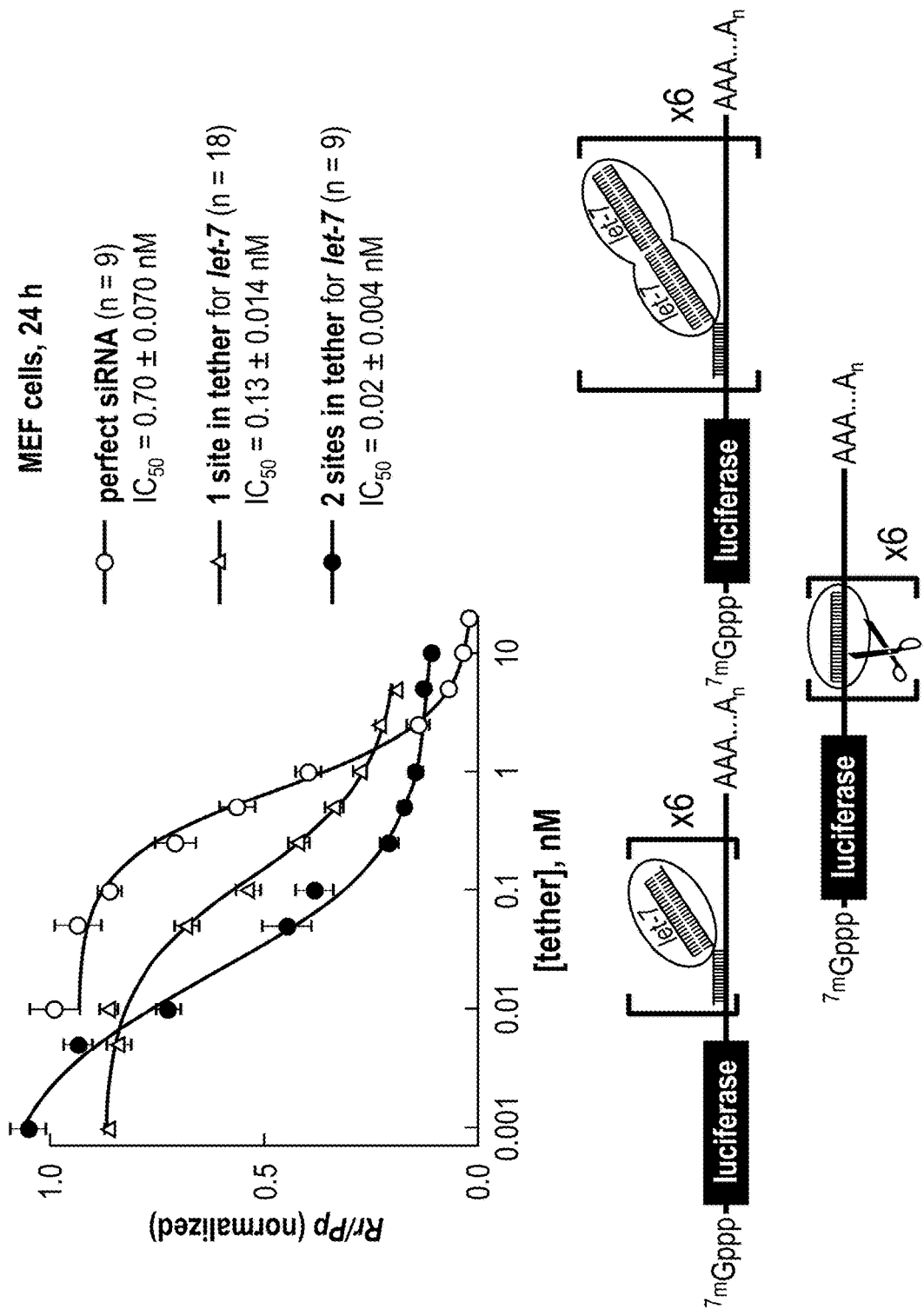
FIG. 5 depicts a dual luciferase reporter assay that demonstrates the efficacy of a tether that contains two sites to which a miRNA can bind.
Figure 6A:
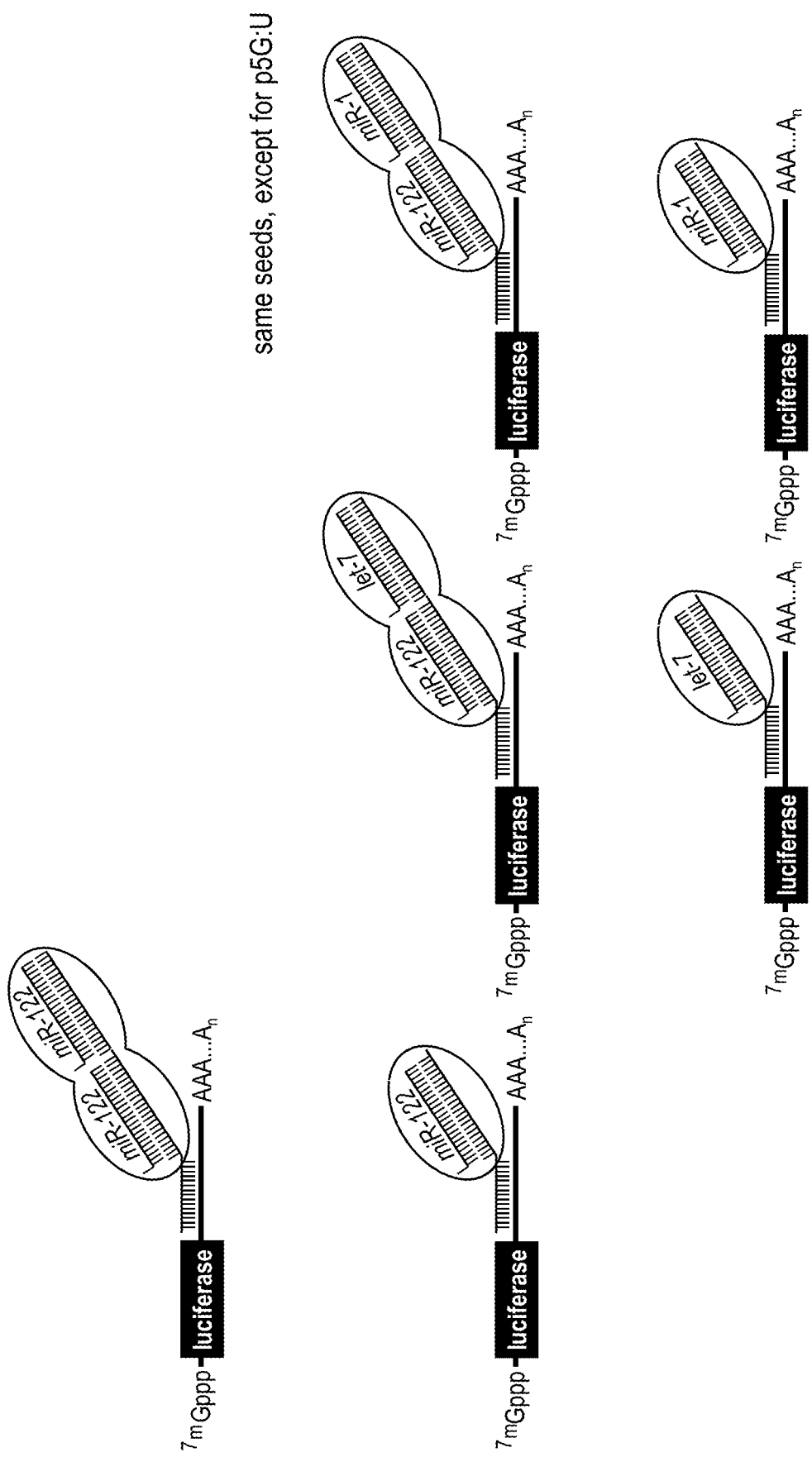
Figure 7:
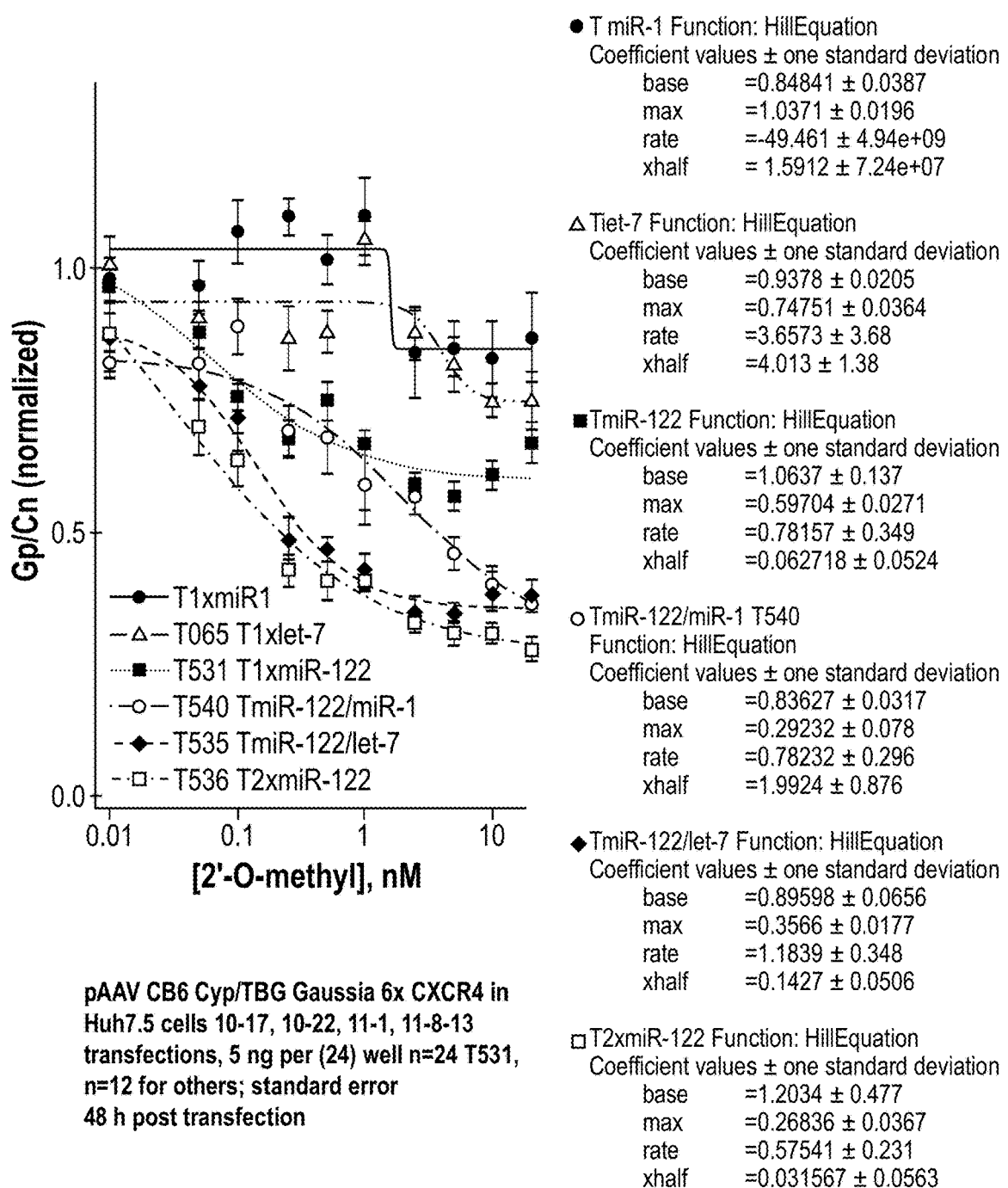
FIG. 7 depicts the greater potency of two-site tethers versus one-site tethers.
Figure 7:
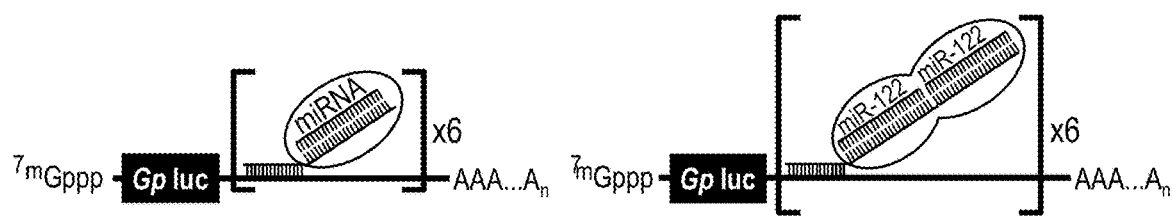

Preliminary studies in MEF cells using a psiCheck2 dual luciferase reporter revealed that a tether that contained two sites to which the miRNA let-7 can bind silenced the luciferase target gene with a 5-fold lower IC50 than that of a tether that can only bind a single let-7 (IC50=0.02±0.004 nM versus 0.13±0.014 nM) (FIG. 5). It is not known if both let-7 binding sites in a tether are simultaneously occupied or if the presence of multiple miRNA-binding sites in the tether increases its effective miRNA occupancy (i.e., the probability that the tether is bound by at least one miRNA is increased by the presence of multiple sites). Silencing of the rAAV expressed reporter target with a tether containing two binding sites for miR-122 was evaluated and compared to a tether containing one miR-122 site. In parallel, tethers were designed that bound miR-122/let-7 and miR 122/miR-1. (FIG. 6). All two-site tethers demonstrated greater potency than one-site tethers. The maximum amount of silencing caused by the miR-122 two-site tether was two-fold lower than that of the miR-122 one site tether (IC50=0.03±0.05 nM versus 0.06±0.05 nM) (FIG. 7). The difference in the effect of increasing the number of miRNA-binding sites on the let-7 and miR-122 tethers likely reflects the difference in promoter strength between psiCheck2 (an SV40 promoter) and the rAAV construct (TBG promoter) or between the miRNA abundance or Argonaute concentration in MEFs versus Huh7.5 cells.

EXAMPLE 3.2

Figure 8:
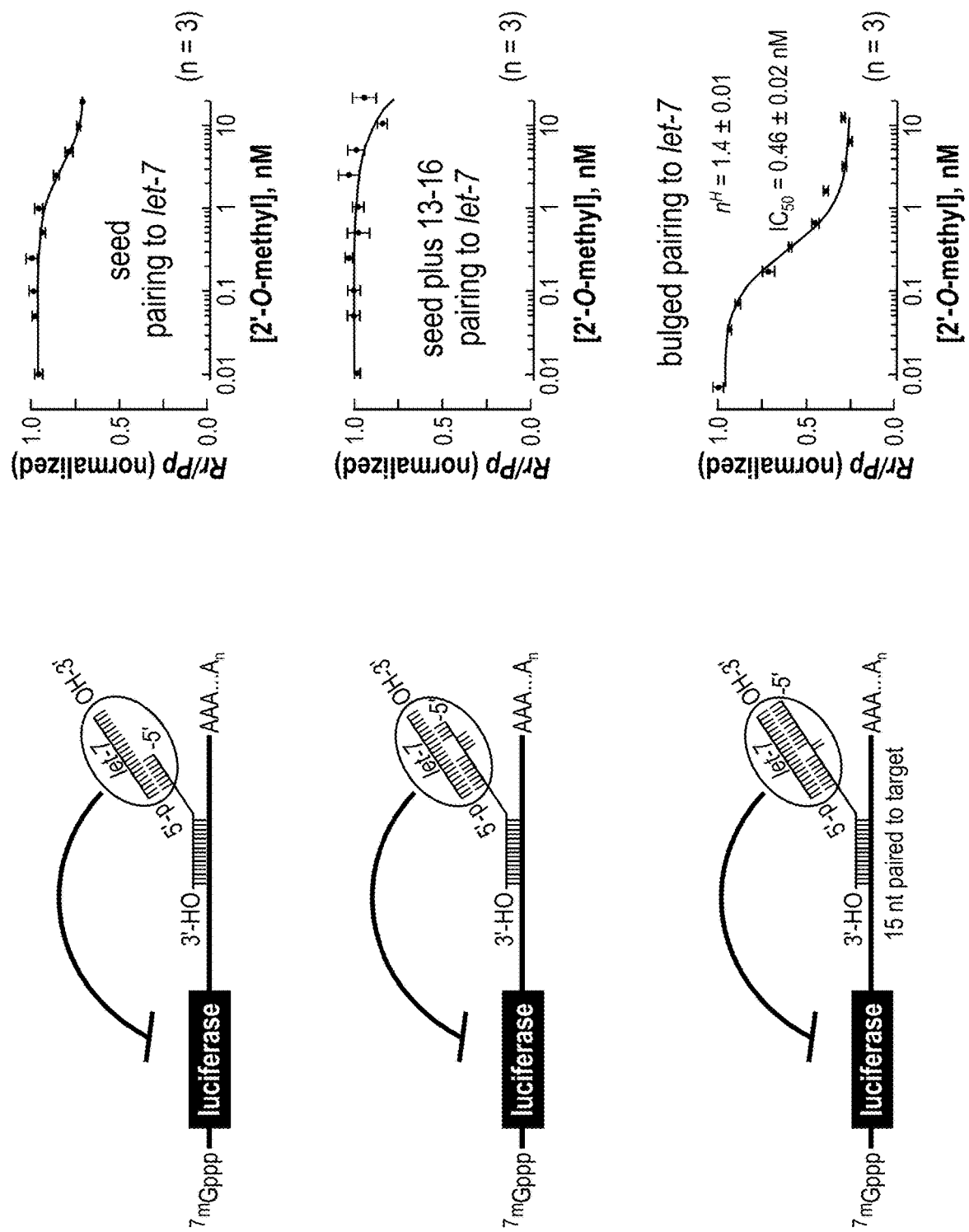
FIG. 8 depicts that the partial pairing between a single let-7 miRNA and its tether is less potent than more complementary pairings.
Figure 9A:
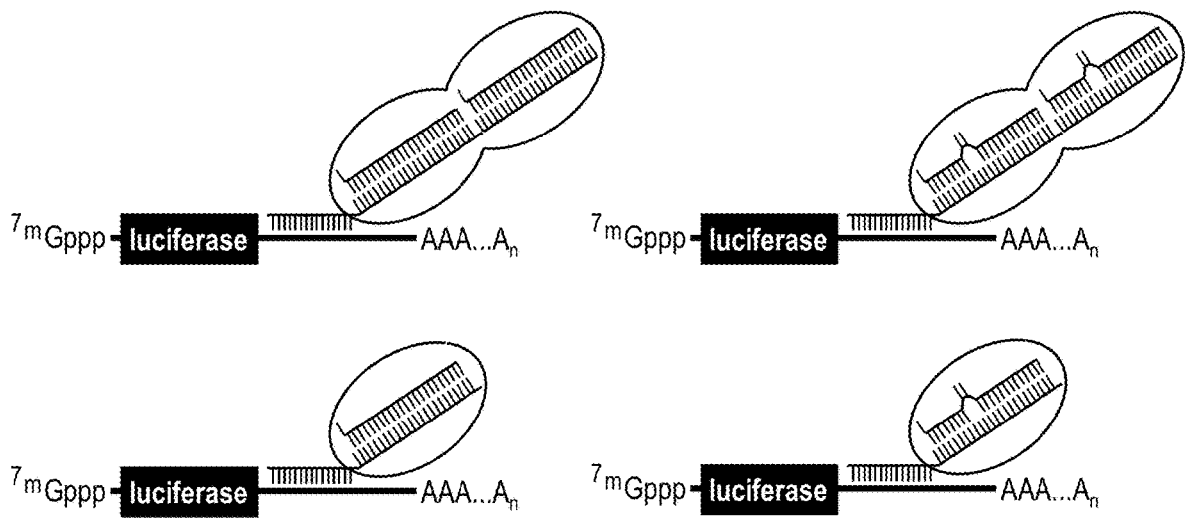
FIGS. 9A-9B depict a schematic of tethers engineered to target one or two miR-122 (FIG. 9A) and the potency of fully complementary versus "bulged" pairings (FIG. 9B).
Figure 9B:
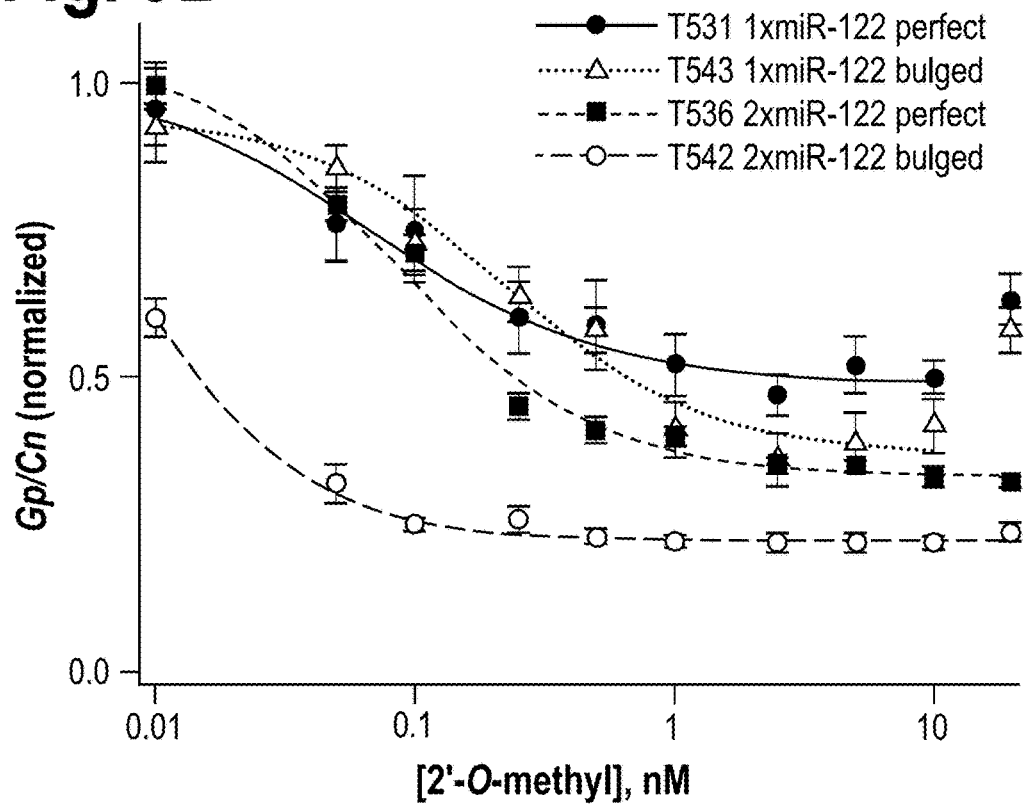
Figure 10A:
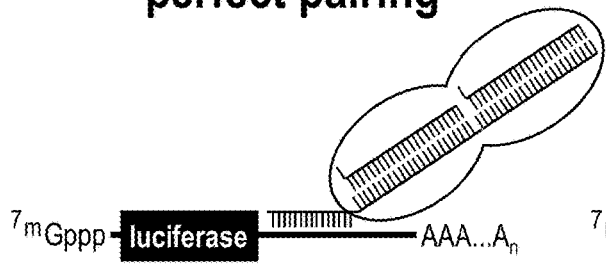
FIGS. 10A-10B depict a schematic of tethers engineered to target one or two miR-122 (FIG. 10A) and the potency of fully complementary versus "bulged" pairings (FIG. 10B).
Figure 10A:
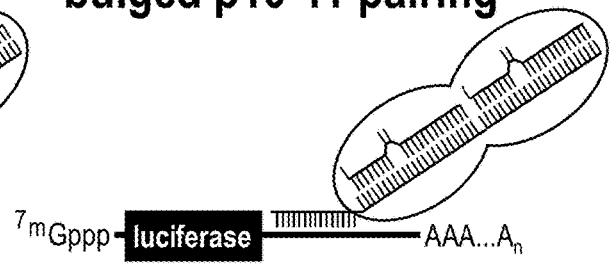
Figure 10A:
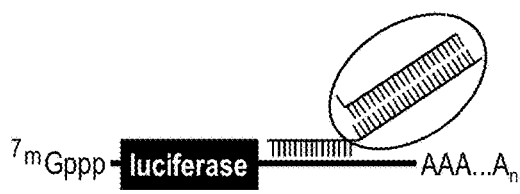
Figure 10A:
Figure 10B:
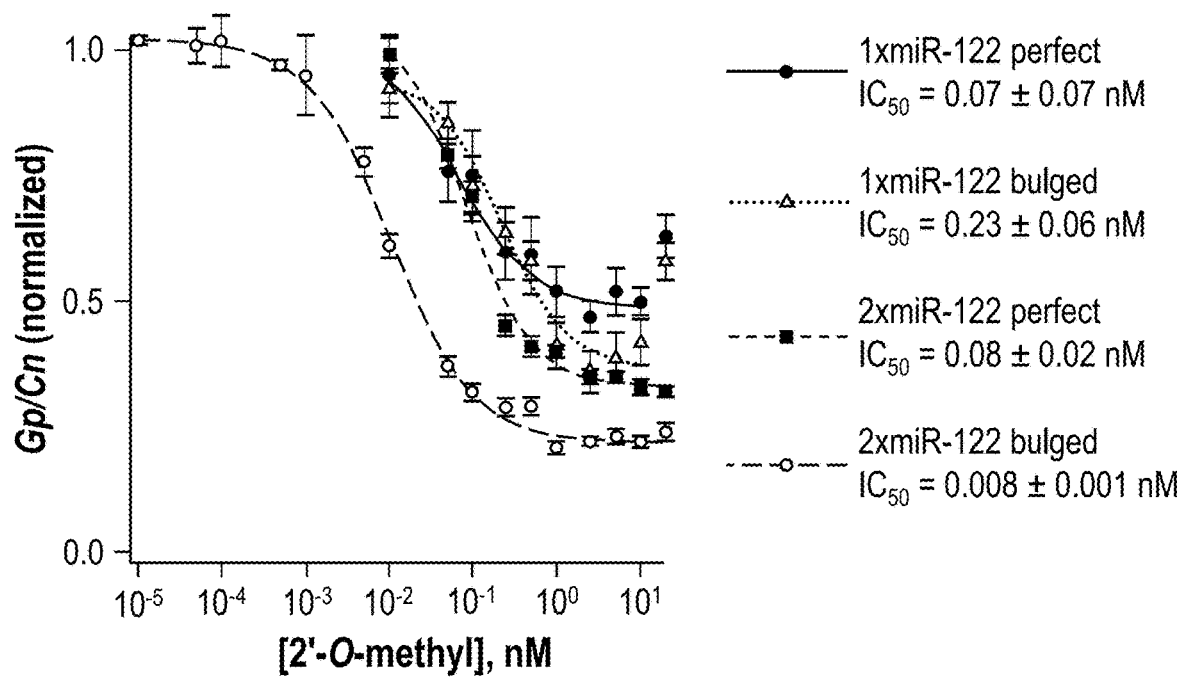

Position-Specific Requirements for Nucleotide Pairing or Mismatches between miRNA or siRNA and Target RNA While therapeutic strategies to silence genes by RNAi rely on the catalytic cleavage of target mRNAs by exogenously supplied small interfering RNAs bound to mammalian Argonaute 2, oligonucleotide tethers do not require the catalytic function of an Argonaute protein for gene silencing. This permits tether sequences to be modified to create a more favorable geometry of mismatches between the tether and its target miRNA to promote the pairing and retention of Argonaute proteins. Preliminary studies revealed that partial pairing between let-7 miRNA and its tether is less potent than more complementary pairings (FIG. 8). Interestingly, a tether with mismatch at nucleic acid positions 9-10 (i.e., a "bulged pairing") of the let-7 miRNA displayed the greatest potency (IC50=0.46±0.02 nM versus >20 nM). To determine whether bulged pairings produced similar results in tethers targeting other miRNAs, tethers were engineered to target one or two miR-122, either perfectly or with mismatches at nucleotide positions 10-11 (p10-11) of miR-122 (FIG. 9). Consistent with previous results, tethers targeting two miR-122 were more potent than tethers targeting one miR-122 (IC50=0.008±0.001 nM and 0.08±0.02 nM versus 0.23±0.06 nM and 0.07±0.07 nM), and in the case of the tethers targeting two miR-122, the tether containing the p10-11 bulge was 10 times more potent than the tether with perfect pairing complementarity (IC50=0.008±0.001 nM and 0.08±0.02 nM) (FIGS. 10B and 11B).

Since a seed only and a fully complementary miRNA: target pairing associate and dissociate at similar rates, a particular geometry of tether pairing was sought that can increase the amount time that a miRNA:RISC is bound by the tether oligonucleotide. In order to pair completely to the target, an Argonaute protein must spend energy to force propagation of pairing from the seed region through the central region of the miRNA, pairing that is functionally irrelevant in the context of mammalian Argonaute proteins 1, 3 and 4, because they lack the catalytic capacity and cannot cleave their targets. Allowing the miRNA to be unpaired at the central region reduces the energy required and may eliminate a conformational shift in the structure of an Argonaute protein that is required to pair to a target beyond the seed region at 3' supplementary region, thus making it more likely that the protein will remain bound to the tether.

Previous literature reported on the computational prediction of miRNA targets and analysis of conserved (in 5 different animal genomes) miRNA seed matches in target mRNAs and revealed a modest conservation of a preference for an adenosine nucleotide at the position that pairs to position 9 of a miRNA (t9A) (Lewis et al., 2005). A separate, more recent published report described locked nucleic acid miRNA inhibitors, i.e., anti-miRs, with the ability to inhibit miRNA-33a and miRNA-33b (Rottiers et al., 2013; distributed by PDZ in email dated 11-25-2013). In this report, an anti-miR that contains an adenosine at the position that pairs to position 9 of the miRNA-33a has a higher potency for inhibition of the miRNA than an anti-miR that inhibits miRNA-33b which contains a guanosine at the position that pairs to position 9 of the miRNA-33b. The authors do not remark on the identity of the nucleotide in this position with respect to conferring increased potency. However, the implication of nucleotide identity at this position as reported in FIG. 1b from Rottiers et al. is consistent with the Lewis et al. publication for modest conservation of t9A in predicted miRNA targets.

Figure 11A:
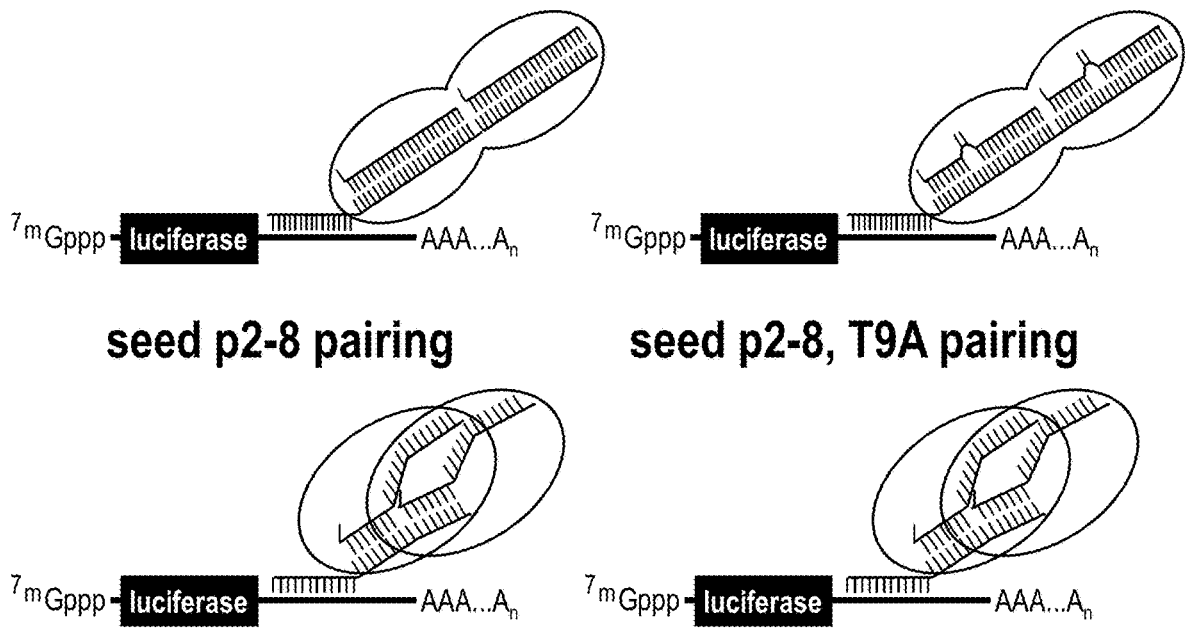
FIGS. 11A-11B depict a schematic of tethers engineered to contain "bulged" pairings (FIG. 11A) and the potency of tethers containing a p10-11 "bulge" (FIG. 11B).
Figure 11B:
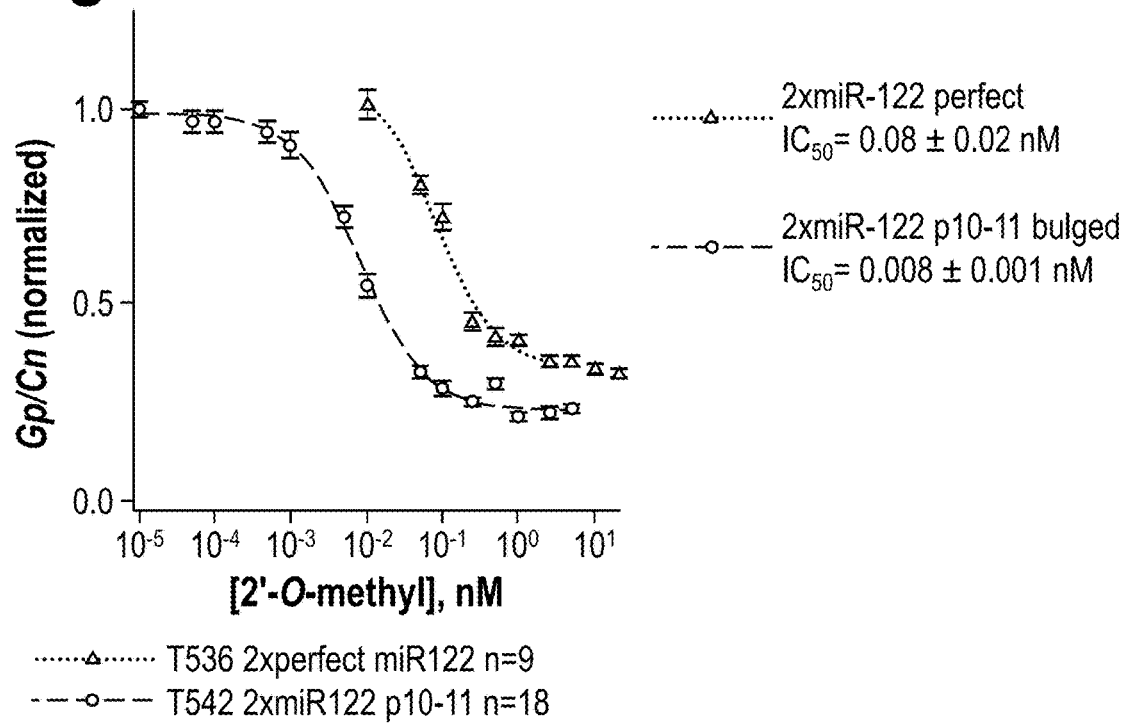
Figure 12A:
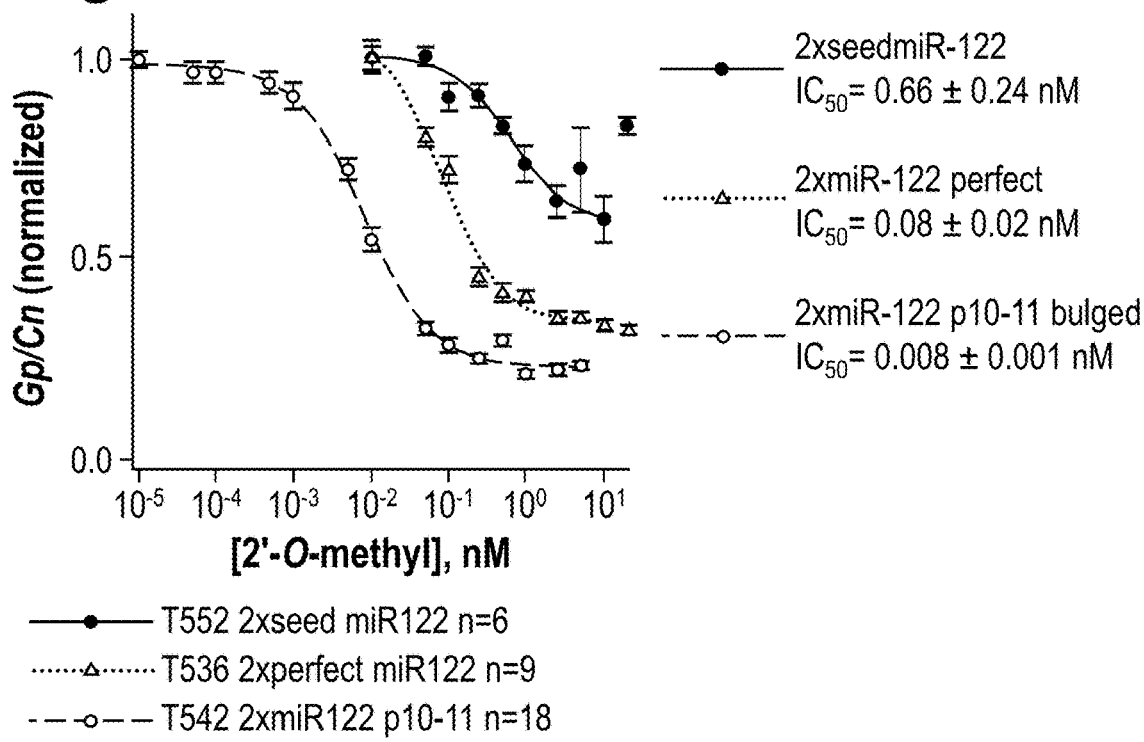
FIGS. 12A-12B depicts the potency of tethers containing a p10-11 "bulge" compared to perfectly complementary tethers or seed only tethers (FIG. 12A) and tethers containing a seed plus T9A (FIG. 12B).
Figure 12B:
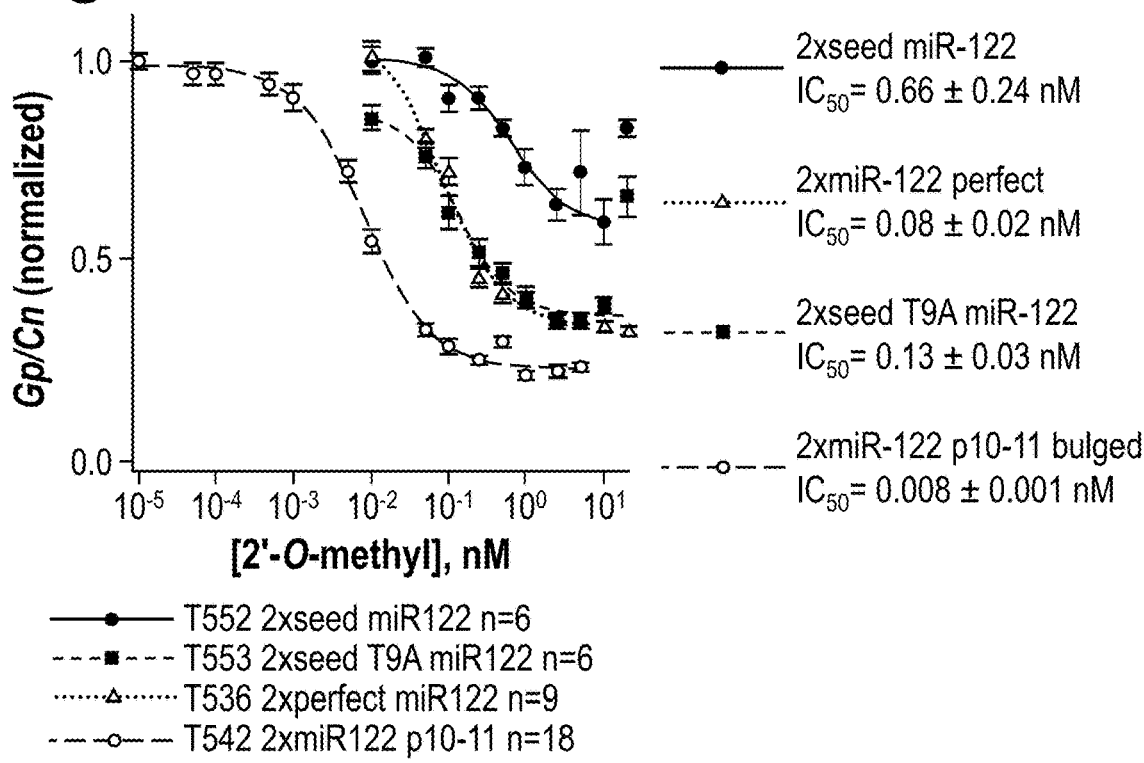
Figure 13A:
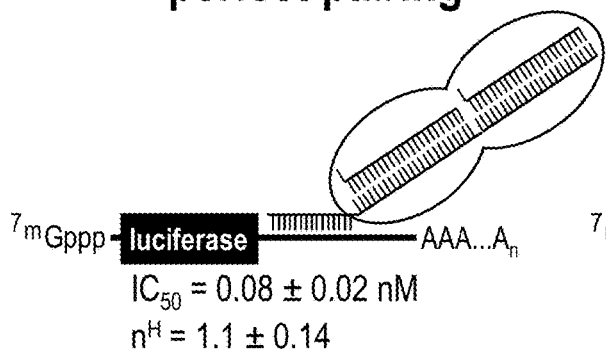
FIGS. 13A-13B depict the potency of tethers designed with perfect complementarity to their miRNA targets versus tethers with "bulged" pairings.
Figure 13A:
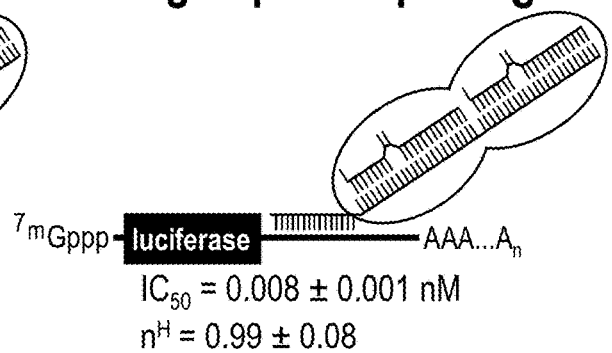
Figure 13A:
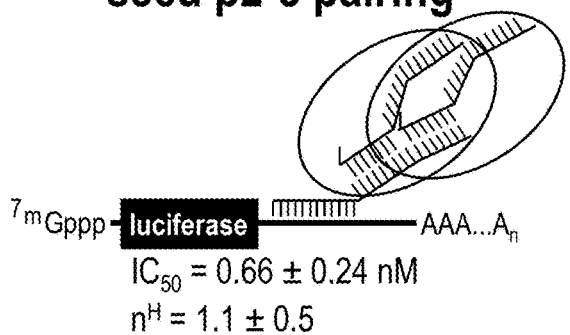
Figure 13A:
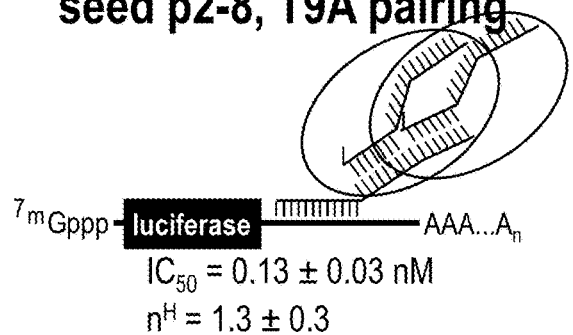
Figure 13B:
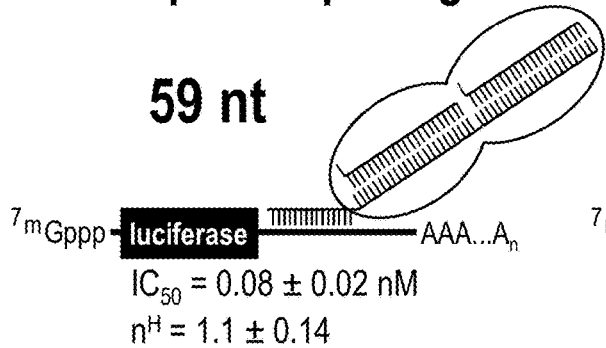
Figure 13B:
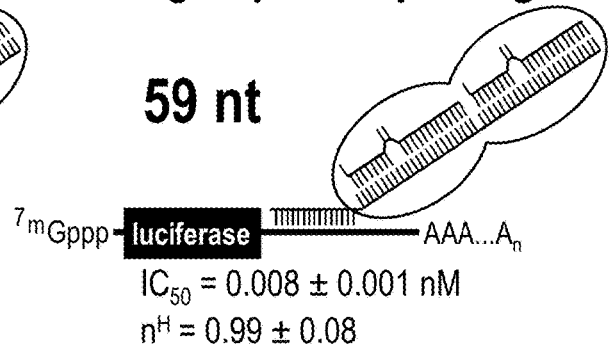
Figure 13B:
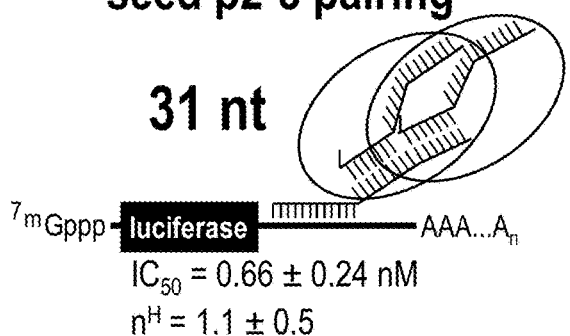
Figure 13B:
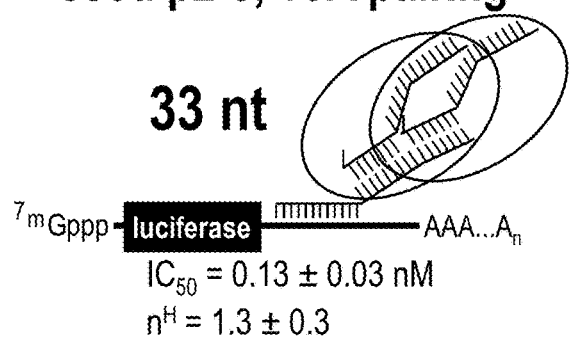
Figure 14B:
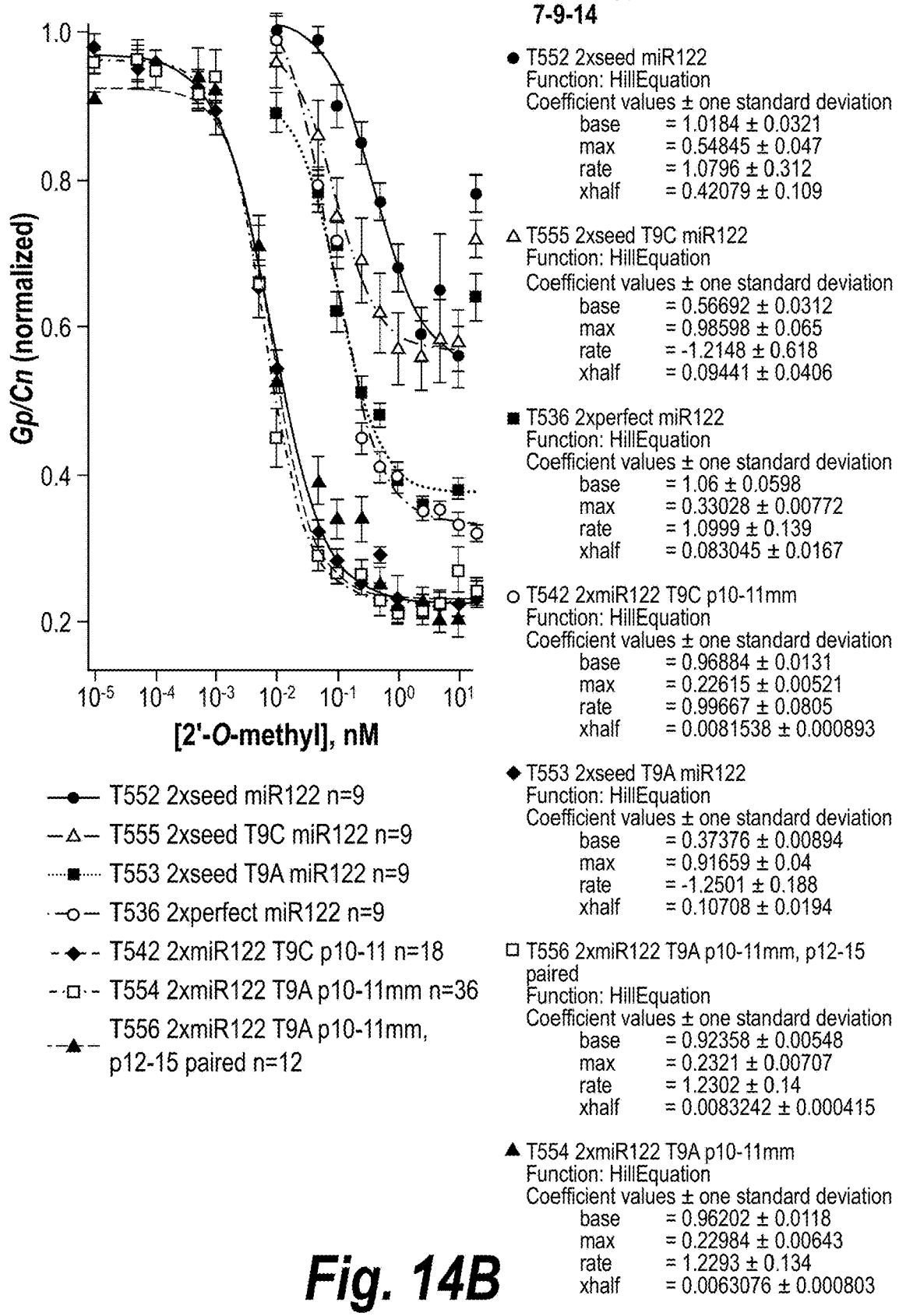

To determine whether Argonaute binding and retention could be promoted or enhanced by tether sequences that contain an adenosine at the position across from position 9 of an miRNA, regardless of whether or not the position forms a Watson-Crick pair to the miRNA, a tether was engineered to contain an adenosine nucleotide in the tether sequence that pairs to position 9 of miRNA-122 (seed p2-8, T9A) (FIG. 11). A two-fold greater potency was observed in the adenosine-containing tether than when the tether contained a cytosine that could base pair to the guanosine at position 9 of miRNA-122 (FIG. 12B and FIG. 14A). These and subsequent experimental data (FIGS. 13-14) show that this specific combination of pairing (i.e., number of complementary nucleotides) and the number and location of mismatches confer extreme potency for silencing to the tether oligonucleotides.

Current strategies require nanomolar concentrations of a synthetic oligonucleotide to effectively inhibit or block miRNA function in mammalian cells. These data demonstrate that a distinct combination of Watson-Crick pairing and mismatches between miRNA-122 and a tether oligonucleotide resulted in a more than 10-fold higher potency, ~2-4 picomolar, for gene silencing than previous versions of the tether. This potency is 10-fold greater than the nanomolar amounts required for an antisense oligonucleotide anti-miR that pairs only with the seed of a miRNA. These data confirm that a tether containing sequence that creates a specific geometry of pairing to a small RNA guide in a mammalian Argonaute protein has an extreme potency for silencing upon binding of a target mRNA, compared to fully complementary or seed only pairing between a tether and a miRNA.

EXAMPLE 3.3

Multiple Argonaute Proteins Support Tether Silencing

Figure 21:
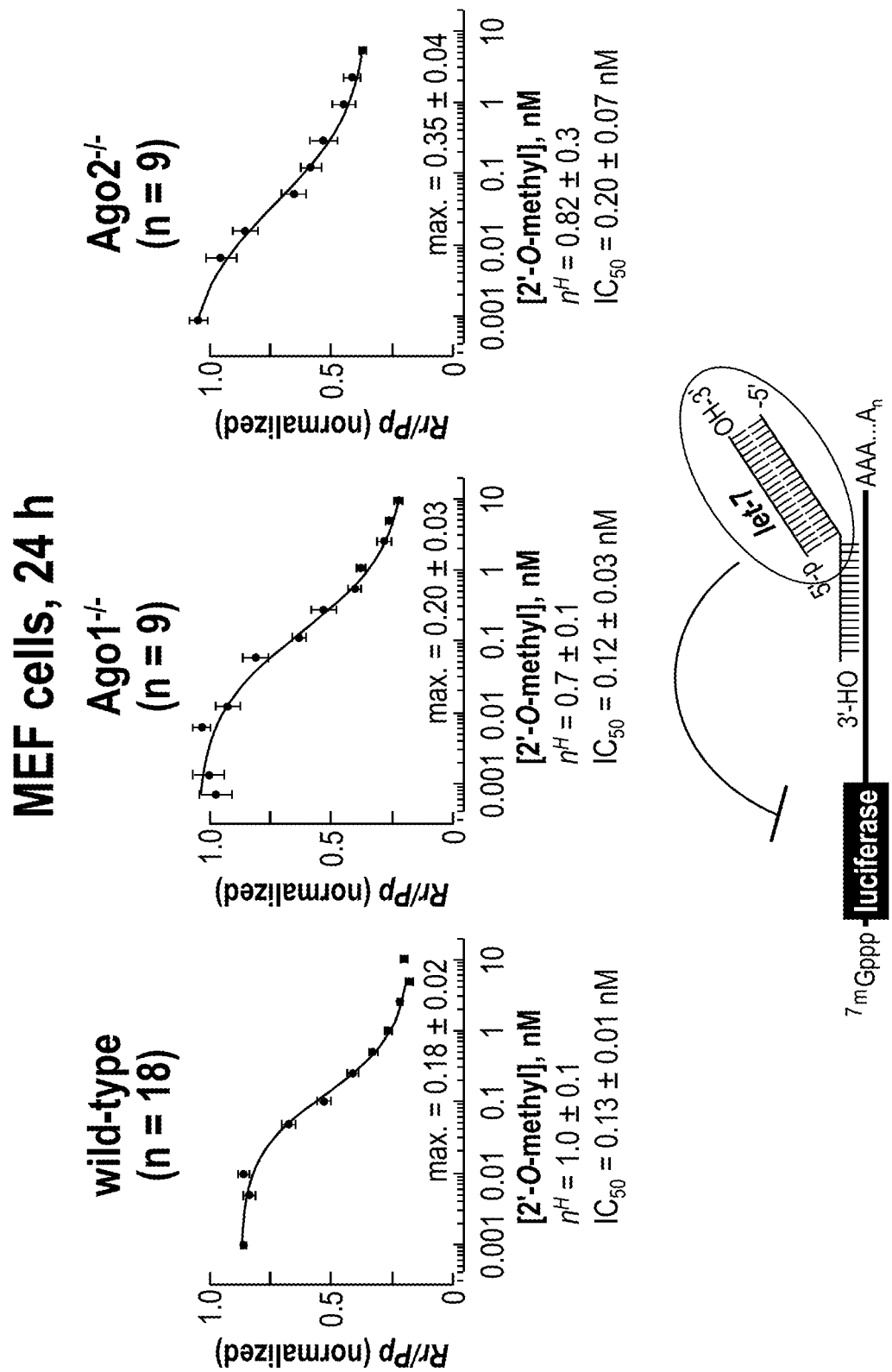
FIG. 21 shows silencing of Renilla luciferase reporter containing 6 sites for a tether to bind in its 3'UTR in MEF cells that are wild type, lacking Argonuate1 protein or lacking Argonaute2 protein. Silencing by a tether does not require the catalytic function of Argonaute2 since a tether that recruits let-7 microRNA can still silence the Renilla luciferase reporter in MEF cells that do not have Argonaute2 protein.

Silencing by siRNAs depends upon the catalytic function of Argonaute2 in order to cleave the target mRNA. Silencing by a tether does not require the catalytic function of Argonaute2 since a tether that recruits let-7 microRNA can still silence the Renilla luciferase reporter in MEF cells that do not have Argonaute2 protein. FIG. 21: Silencing of Renilla luciferase reporter containing 6 sites for a tether to bind in its 3'UTR in MEF cells that are wild type, lacking Argonautel protein or lacking Argonaute2 protein.

EXAMPLE 3.4

Figure 15:
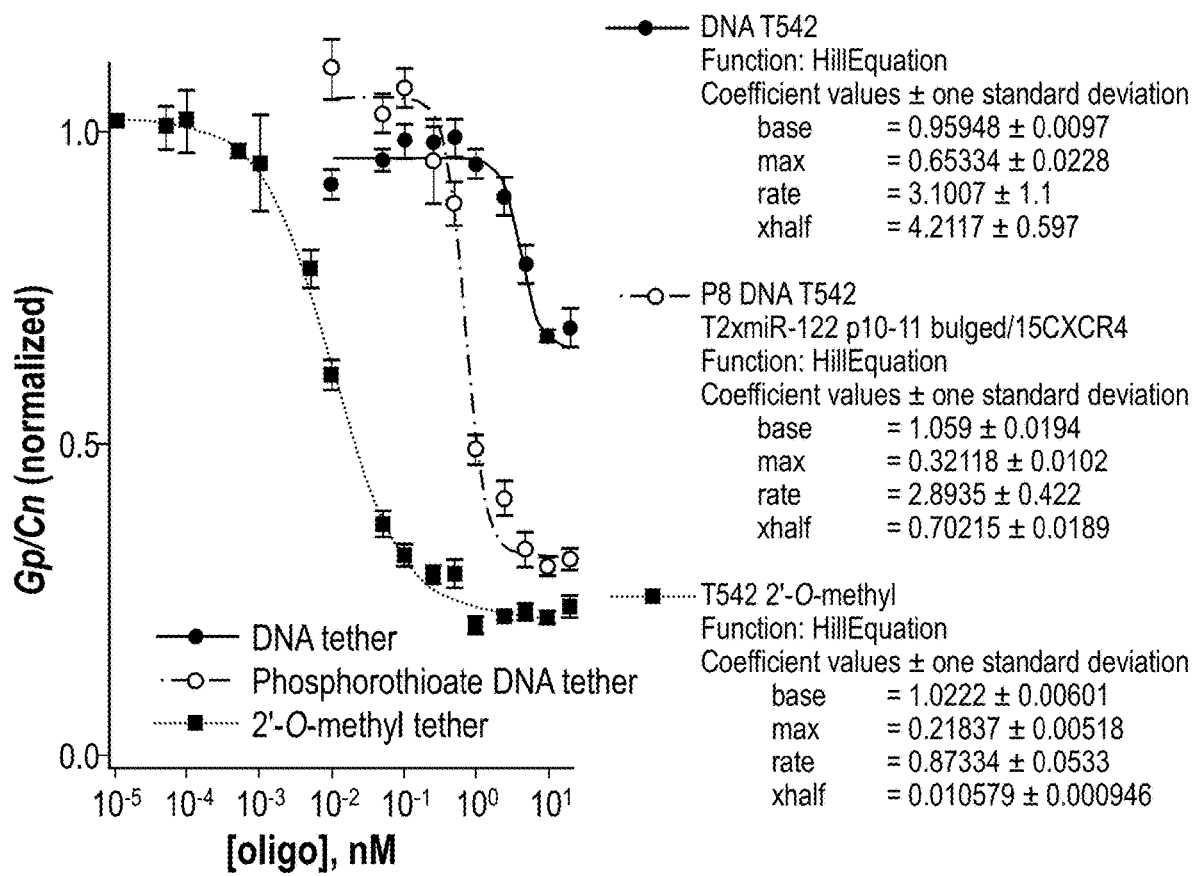
FIG. 15 depicts the potency of S-oligo modified tethers engineered to target miR-122 to CXCR4 mRNA.

Position-Specific Requirements for Nucleotide Pairing or Mismatches between miRNA or siRNA and Target RNA Phosphorothioates (or S-oligos) are an oligonucleotide variant in which one of the nonbridging oxygens is replaced by a sulfur. The sulfurization of the internucleotide bond dramatically reduces the action of endo-and exonucleases. In addition, S-oligos have demonstrated an increased potential for crossing the cell membranes. S-oligo modified tethers were engineered to recruit miR-122 to a Gaussia luciferase reporter mRNA containing six sites in its 3'UTR ,the vector-based strategy described in FIG. 4. As shown in FIG. 15, S-oligo modified DNA tethers were more potent than unmodified DNA tethers but less potent than 2'-O-methyl modified tethers. This potency is a reflection of the preference of Argonaute proteins to bind RNA over DNA. Mouse AGO2, like all known animal Argonautes, has only been reported to function by binding RNA targets. In fact, kw, for a seed-matched, seed-matched plus supplementary pairing, or a completely complementary DNA target was ~2.3 to 3.3 times faster than the on-rate for the corresponding RNA target (Salomon et al., 2014). However, mouse AGO2-RISC does not remain stably bound to the DNA, and dissociates, on average, just ~2.4 s ($k_{off}$=0.41±0.09 s$^{-1}$) after binding a seed-matched DNA target. The >110-fold faster dissociation of AGO2-RISC from DNA compared to RNA supports the view that even when acting in the nucleus, eukaryotic RISCs bind nascent transcripts, not single-stranded DNA (Buhler et al., 2006; Sabin et al., 2013).

EXAMPLE 4

Recruiting multiple miRNAs In Vivo

Figure 16A:
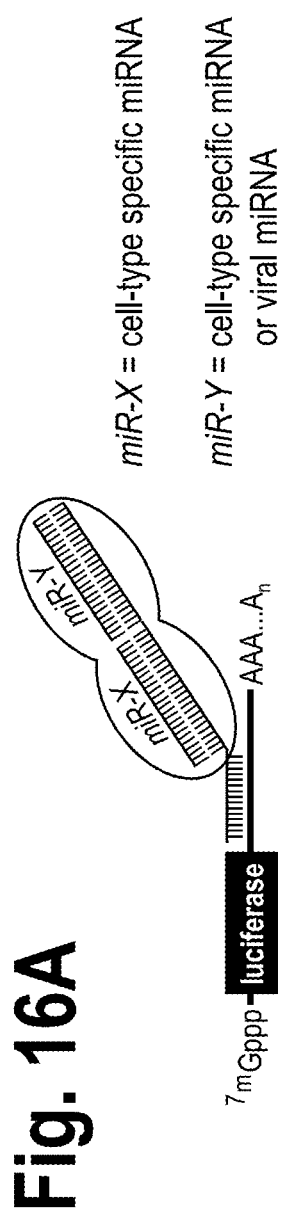
FIGS. 16A-16B depict.
Figure 16B:
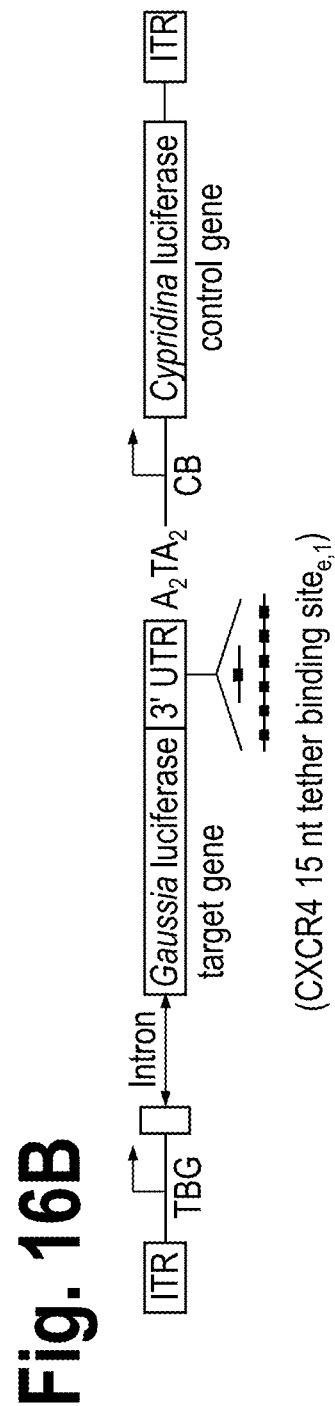
Figure 17:
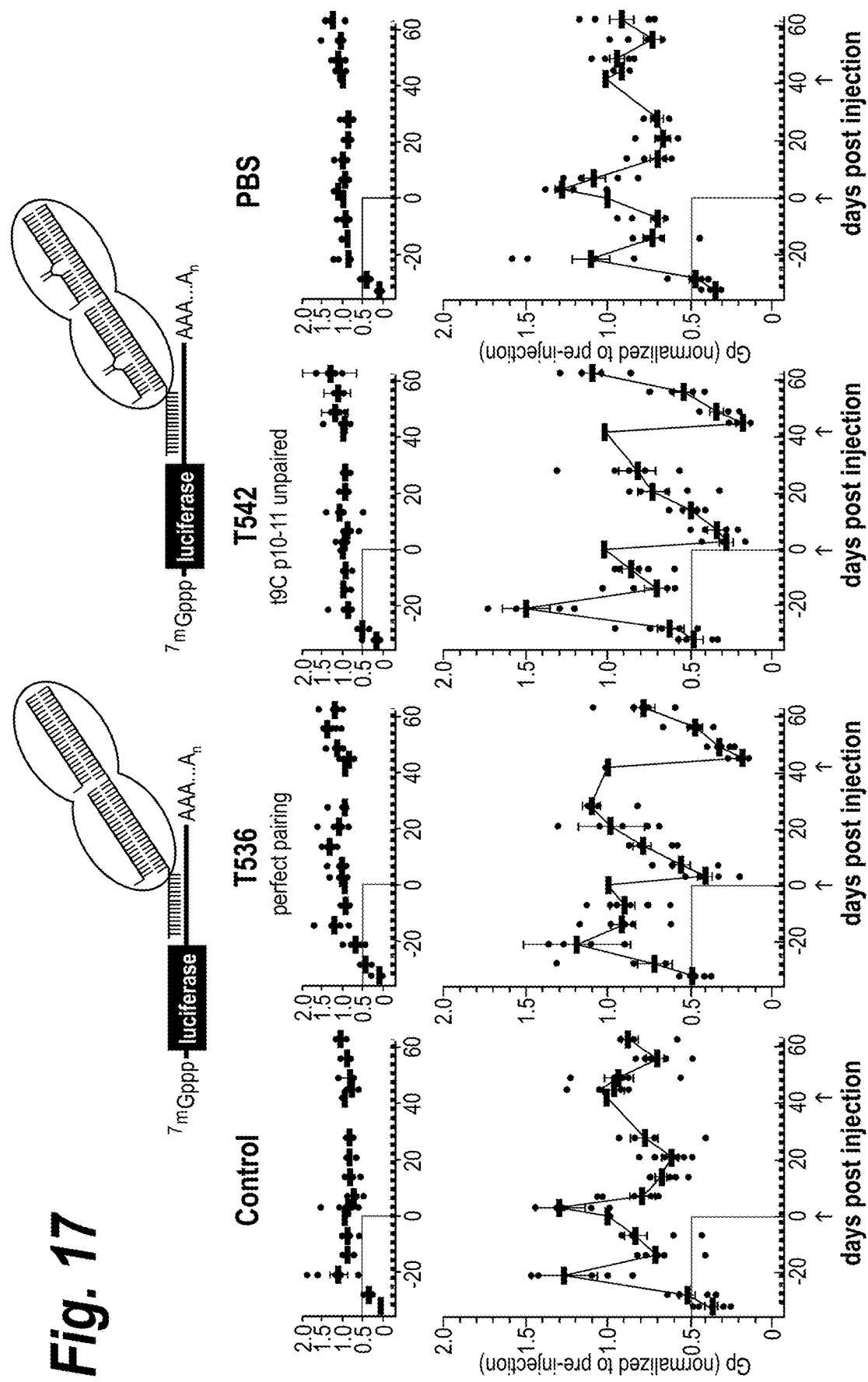
FIG. 17 depicts the in vivo efficacy of two separate tethers T536 (perfectly paired to two miR-122) or T542 (mismatched at p10-11 to two miR-122) to silence expression of Gaussia luciferase by 60-80% in the liver at a dose of 1.5 mg/kg in two separate doses, arrows indicate dose day.

To test whether oligonucleotide tethers that bind two endogenous miRNAs could suppress the expression of the Gaussia luciferase reporter target mRNA in vivo, tethers were engineered to bind two endogenous miRNAs and tested in the rAAV secreted dual luciferase reporter that was created to monitor gene silencing over time in living mice (FIG. 16B). Mice were infected with 10^10 rAAV particles which was sufficient to detect luciferase activity in serum as demonstrated in FIG. 16C, and assayed for luciferase expression at 3-weeks post-infection. Suppression of the Gaussia luciferase target activity, but no the control Cypridina luciferase was observed three days after injection of either experimental tether but not in PBS control-injected mice. FIG. 17 shows that two separate tethers, T536 (perfectly paired to two miR-122) or T542 (mismatched at p10-11 to two miR-122) silenced Gaussia luciferase expression by 60-80% in the liver at a dose of 1.5 mg/kg in two separate doses.

EXAMPLE 5

Tethering to a Single 15 nt Site in APOC3

APOC3 is involved in cholesterol biosynthesis. To test whether tethers could inhibit expression of APOC3, tethers were designed to bind a single site, 15 nt long in the 3'UTR of the APOC3 transcript and the seed regions and positions 12-16 or 12-17 of two miR122s (FIG. 18A). Huh7.5 cells were transfected with 10-150 nM of either tether oligo and APOC3 mRNA was quantified 48 hours post-transfection by qRT-PCR. As shown in FIG. 18B and FIG. 18C, the miR-122 tethers silenced APOC3 gene in human hepatocytes by 50%.

EXAMPLE 6

Silencing APOC3 and Reducing Triglycerides

As shown in FIG. 19A, expression of Apolipoprotein C-III (referred to herein as ApoC-III or APOC3) was silenced in mouse liver, a clinically relevant target in cardiovascular and metabolic disease. ApoC-III is produced in the liver and inhibits lipoprotein lipase which regulates the level of serum triglycerides. Subjects who do not produce ApoC-III have lower levels of triglycerides and lower risk of cardiovascular disease, and patients with lower levels of ApoC-III and triglycerides exhibit lower cardiovascular event rates. Conversely, subjects with elevated levels of ApoC-III have increased dyslipidemia associated with multiple metabolic abnormalities, such as insulin resistance or metabolic syndrome (MetS), or both.

Figure 19B:
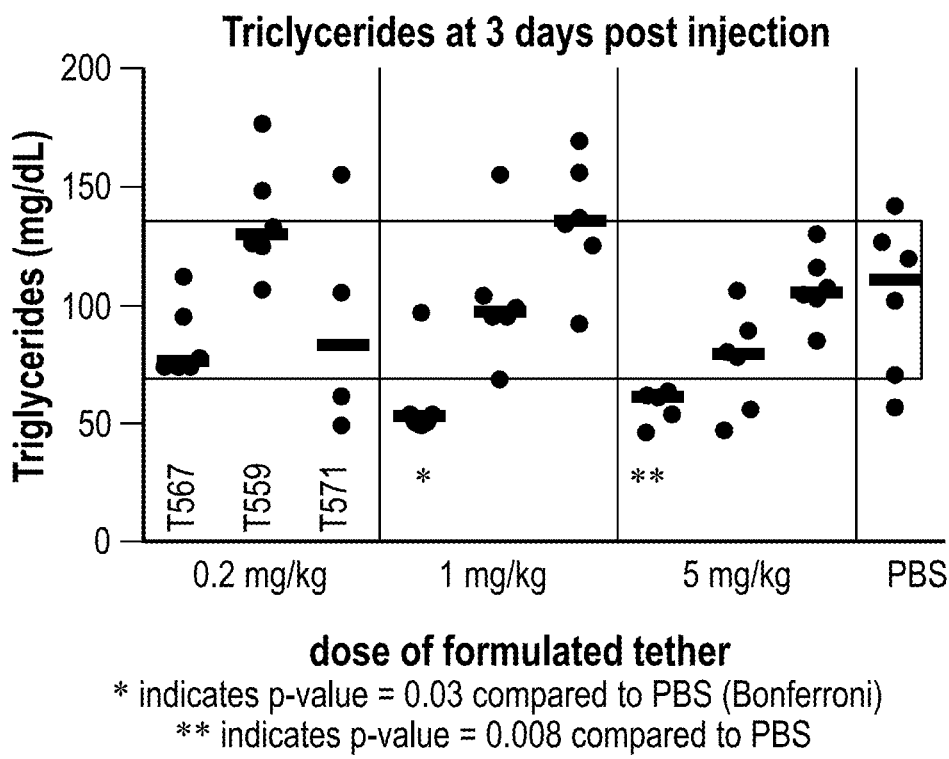
FIG. 19B shows serum triglyceride levels (mg/dL) in mice 3 days after they were treated with 3 different doses (0.2 mg/kg, 1 mg/kg, or 5 mg/kg) of a tether (T567: experimental APOC3/miR-122 tether, T559: miR-122 inhibition control tether, T571: APOC3 antisense silencing control tether).
Figure 19C:
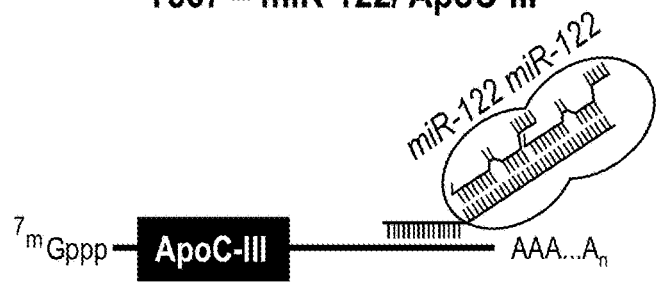
FIG. 19C shows a diagram of the tethers used in vivo in FIG. 19A and FIG. 19B. T567: experimental APOC3/miR-122 tether, T559: miR-122 inhibition control tether, T571: APOC3 antisense silencing control tether.
Figure 19C:
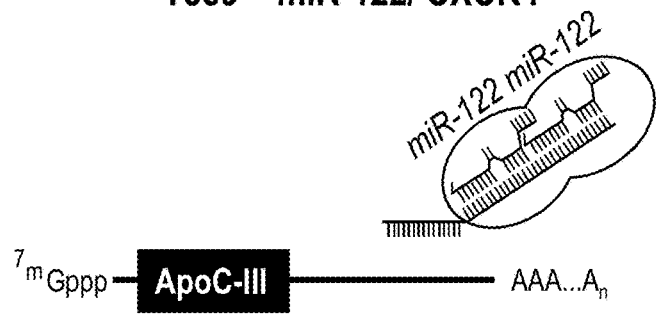
Figure 19C:

As shown in FIG. 19B, with in vivo experiments in mice, bi-functional oligonucleotides reduced serum TG by 50% (a clinically relevant change) compared to control and PBS-treated mice. Unlike ApoC-III ASOs and ApoC-III siRNAs, the bi-functional oligonucleotides (the RNA-modulating agents) described herein tether a microRNA to the mRNA to silence the target. ASOs rely on nucleic acid hybridization to recruit RNase H to cause gene silencing. The constant of dissociation between a microRNA and Argonaute protein (pico-molar) is much lower than that of RNase H and ASO target (nano-molar). This means that the RNA-modulating agents described herein allow delivery of much less trigger molecule (<1 mg/kg) to cause silencing than a current phase III ASO targeting ApoC-III (300 mg/kg). The RNA-modulating agents described herein are single-stranded and distinct from gene silencing by double-stranded siRNAs which can only be modified using nuclease-resistant chemistries compatible with the cellular RNAi machinery. Furthermore, the RNA-modulating agents described herein are cell-type specific: they are designed to silence the target mRNA only in cells that contain both the specified microRNA and the target. This prevents silencing of the target in unintended tissues.

We claim:

1. A method of modulating expression of a target protein in a cell, the method comprising delivering into the cell an RNA-modulating agent comprising an mRNA binding sequence that is complementary to a portion of a target mRNA sequence encoding the target protein, linked to two or more miRNA binding sequences, wherein one or more of the miRNA binding sequences are complementary to at least positions 2 to 8 of an miRNA, but not complementary to positions 10 and 11 of the miRNA, wherein the RNA-modulating agent modulates the translation of the target protein, and wherein the target mRNA encodes a protein that causes a disease or disorder.

2. The method of claim 1, wherein the target mRNA is APOC3.

3. The method of claim 1, wherein the target mRNA is SOD1.

4. The method of claim 1, wherein one or more of the miRNA binding sequences are not complementary to position 1 of the miRNA.

5. The method of claim 1, wherein the mRNA binding sequence is flanked by miRNA binding sequences in the RNA-modulating agent.

6. The method of claim 1, wherein the miRNA binding sequences are linked to the 5' end of the mRNA binding sequence.

7. The method of claim 1, wherein the miRNA binding sequences are linked to the 3' end of the mRNA binding sequence.

8. The method of claim 1, wherein the miRNA is a tissue specific miRNA.

9. The method of claim 1, wherein the miRNA is selected from the group consisting of miR122, miR-1, let-7, miR-103, miR-107 miR-216, miR-375, miR-124, miR-125, miR-128, miR-132, miR-134, miR-135, miR-138, miR-153, miR-143, miR-194, miR-133a, miR-206, miR-208, miR-142-3p, miR-143-5p, miR-181, miR-195, miR-221, miR-222, miR-192, miR-194, miR-204, miR-215, miR-30b, miR-30c, miR-122a, miR-152, miR-199, miR-215, miR-130, miR-24, miR-32, miR-189, miR-127, miR-150, miR-151, miR-212, miR-148, miR-204, and miR-378.

10. The method of claim 1, wherein the miRNA is a viral microRNA.

11. The method of claim 1, wherein the target mRNA encodes a protein that is overexpressed or overactive.

* * * * *

SEQUENCE LISTING

```
<160> NUMBER OF SEQ ID NOS: 6

<210> SEQ ID NO 1
<211> LENGTH: 22
<212> TYPE: RNA
<213> ORGANISM: Artificial Sequence
<220> FEATURE:
<223> OTHER INFORMATION: synthetic oligonucleotide

<400> SEQUENCE: 1
uggaauguaa agaaguaugu au                                              22

<210> SEQ ID NO 2
<211> LENGTH: 22
<212> TYPE: RNA
<213> ORGANISM: Artificial Sequence
<220> FEATURE:
<223> OTHER INFORMATION: synthetic oligonucleotide

<400> SEQUENCE: 2
uggaguguga caauggug uu ug                                             22

<210> SEQ ID NO 3
<211> LENGTH: 37
<212> TYPE: RNA
<213> ORGANISM: Artificial Sequence
<220> FEATURE:
<223> OTHER INFORMATION: synthetic oligonucleotide

<400> SEQUENCE: 3
auacauacuu cuuuacauuc caccgguguu agcuuug                              37

<210> SEQ ID NO 4
<211> LENGTH: 37
<212> TYPE: RNA
<213> ORGANISM: Artificial Sequence
<220> FEATURE:
<223> OTHER INFORMATION: synthetic oligonucleotide

<400> SEQUENCE: 4
caaacaccau ugucacacuc caccgguguu agcuuug                              37

<210> SEQ ID NO 5
<211> LENGTH: 46
<212> TYPE: RNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (1)..(46)
<223> OTHER INFORMATION: 2'-O-methyl

<400> SEQUENCE: 5
ccauuagaac acuccaccau uagaacaccc aagcuucuug uccagc                    46
```

```
<210> SEQ ID NO 6
<211> LENGTH: 48
<212> TYPE: RNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (1)..(48)
<223> OTHER INFORMATION: 2'-O-methyl

<400> SEQUENCE: 6
accauuagaa cacuccaacc auuagaaccu ccaagcuucu uguccagc                48
```